US012723284B2

(12) United States Patent
An et al.

(10) Patent No.: US 12,723,284 B2
(45) Date of Patent: Sep. 1, 2026

(54) COMPOSITION FOR DIAGNOSING SARS-CoV-2, KIT, AND METHOD FOR DIAGNOSING SARS-CoV-2 BY USING SAME

(71) Applicant: GENOMICTREE, INC., Daejeon (KR)

(72) Inventors: Sunghwan An, Daejeon (KR); Myung Soon Kim, Daejeon (KR)

(73) Assignee: GENOMICTREE, INC., Daejeon (KR)

( * ) Notice: Subject to any disclaimer, the term of this patent is extended or adjusted under 35 U.S.C. 154(b) by 921 days.

(21) Appl. No.: 17/759,067

(22) PCT Filed: Mar. 5, 2021

(86) PCT No.: PCT/KR2021/002735
§ 371 (c)(1),
(2) Date: Jul. 19, 2022

(87) PCT Pub. No.: WO2021/177773
PCT Pub. Date: Sep. 10, 2021

(65) Prior Publication Data

US 2023/0057087 A1 Feb. 23, 2023

(30) Foreign Application Priority Data

Mar. 6, 2020 (KR) ........................ 10-2020-0028155

(51) Int. Cl.
*C12Q 1/68* (2018.01)
*C12Q 1/6851* (2018.01)
*C12Q 1/70* (2006.01)

(52) U.S. Cl.
CPC ............. *C12Q 1/70* (2013.01); *C12Q 1/6851* (2013.01); *C12Q 2531/10* (2013.01)

(58) Field of Classification Search
None
See application file for complete search history.

(56) References Cited

FOREIGN PATENT DOCUMENTS

| | | | | |
|---|---|---|---|---|
| CN | 1922330 A | 2/2007 | | |
| JP | 2006523460 A | 10/2006 | | |
| KR | 1020060017212 B1 | 2/2006 | | |
| KR | 100891399 B1 | 3/2009 | | |
| WO | 2004096842 A2 | 11/2004 | | |
| WO | 2016179509 A1 | 11/2016 | | |
| WO | 2021016453 A1 | 1/2021 | | |
| WO | WO-2021154828 A1 * | 8/2021 | .............. | A61P 31/14 |
| WO | WO-2021201996 A1 * | 10/2021 | ......... | C12N 15/1131 |

OTHER PUBLICATIONS

Chan et al. (J Clin Microbiol 53:2722-2726) (Year: 2015).*
GenBank NC_045512, Wuhan seafood market pneumonia virus isolate Wuhan-Hu-1, complete genome (15 pages) (Year: 2020).*
Sola et al. (Annu. Rev. Virol. 2015. 2:265-88). (Year: 2015).*
Kim et al. (2020, Cell 181, 914-921) (Year: 2020).*
Yin (Genomics 112 (2020) 3588-3596) (Year: 2020).*
Chan, J. F-W, et al., "Development and Evaluation of Novel Real-Time Reverse Transcription—PCR Assays with Locked Nucleic Acid Probes Targeting Leader Sequences of Human-Pathogenic Coronoviruses", Journal of Clinical Microbiology, 2015, vol. 53, No. 2722-2726, Publisher: JCM.
Huang, C., et al., "Clinical features of patients infected with 2019 novel coronovirus in Wuhan, China", Lancet, 2020, Page(s) https://doi.org/10.1016/S0140-6736(20)30183-5, Publisher: www.thelancet.com.
Imbert, I., et al., "A second, non-canonical RNA-dependent RNA polymerase in SARS Coronovirus", The EMBO Journal, 2006, pp. 4933-4842, vol. 25, No. 20, Publisher: European Molecular Biology Organization.
"Wuhan seafood market pneumonia virus isolate Wuhan-Hu-1, complete genome", NCBI, 2020, Page(s) NC_045512.
Extended European Search Report issued on Mar. 4, 2024 for European Patent Application EP21764053.
Notice of Allowance issued on Dec. 15, 2023 for the Japanese Patent Application 2022-549743.
English Translation of Notice of Allowance issued on Dec. 15, 2023 for the Japanese Patent Application 2022-549743.
Office Action Issued in Japanese Patent Application No. 2022549743 on Aug. 8, 2023.
English Translation of Office Action Issued in Japanese Patent Application No. 2022549743 on Aug. 8, 2023.
Wu, F., et al., "A new coronavirus associated with human respiratory disease in China", Nature, 2020, https://doi.org/10.1038/s41586-020-2008-3, vol. 579.
Genbank, "Severe acute respiratory syndrome coronavirus 2 isolate 2019-nCoV WHU01, complete genome", Genbank Accession No. MN988668, 2020.
Office Action Issued in counterpart Korean Patent Application No. 10-2021-0029217 on Jan. 17, 2023.
English Translation of Office Action Issued in counterpart Korean Patent Application No. 10-2021-0029217 on Jan. 17, 2023.
Search Report issued on Mar. 18, 2026 for Chinese Patent Application 2021800157684.

(Continued)

*Primary Examiner* — Juliet C Switzer
(74) *Attorney, Agent, or Firm* — HULTQUIST IP; Steven J. Hultquist

(57) ABSTRACT

The present invention relates to a composition for diagnosing whether someone has been infected with a novel coronavirus (SARS-CoV-2: Severe acute respiratory syndrome coronavirus 2), a kit comprising the composition, and a method for diagnosing whether someone has been infected with the novel coronavirus by using same. Particularly, the present invention relates to a composition for diagnosing whether someone has been infected with a novel coronavirus, comprising a nucleic acid oligomer capable of specifically amplifying by targeting a leader sequence most abundantly present in cells infected with the novel coronavirus, a kit comprising the composition, and a method for diagnosing whether someone has been infected with the novel coronavirus by using same.

4 Claims, 3 Drawing Sheets

Specification includes a Sequence Listing.

(56) References Cited

OTHER PUBLICATIONS

English Translation of Search Report issued on Mar. 18, 2026 for Chinese Patent Application 2021800157684.
Sola, I., et al., "Continuous and Discontinuous RNA Synthesis in Coronaviruses", Annu. Rev. Virol., 2015, pp. 265-288 (doi: 10.1146/annurev-virology-100114-055218), vol. 2.

* cited by examiner

Coronavirus : 3' co-terminal nested structure inside cell
Leader
Polymerase (RdRP)
Nonstructural
S protein
E protein
M protein
Nucleocapsid (N)
Leader joining
Highest redundancy

【Fig. 1】
RdRP gene
GTGAAATGGTCATGTGTGGCGG CCAGGTGGAACCTCATCAGGAGATGC TATGCTAATAGTGTTTTTAACATTTG
E gene
ACAGGTACGTTAATAGTTAATAGCGT ACACTAGCCATCCTTACTGCGCTTCG ATTGTGTGCGTACTGCTGCAATAT
【Fig. 2】

【Fig. 3】
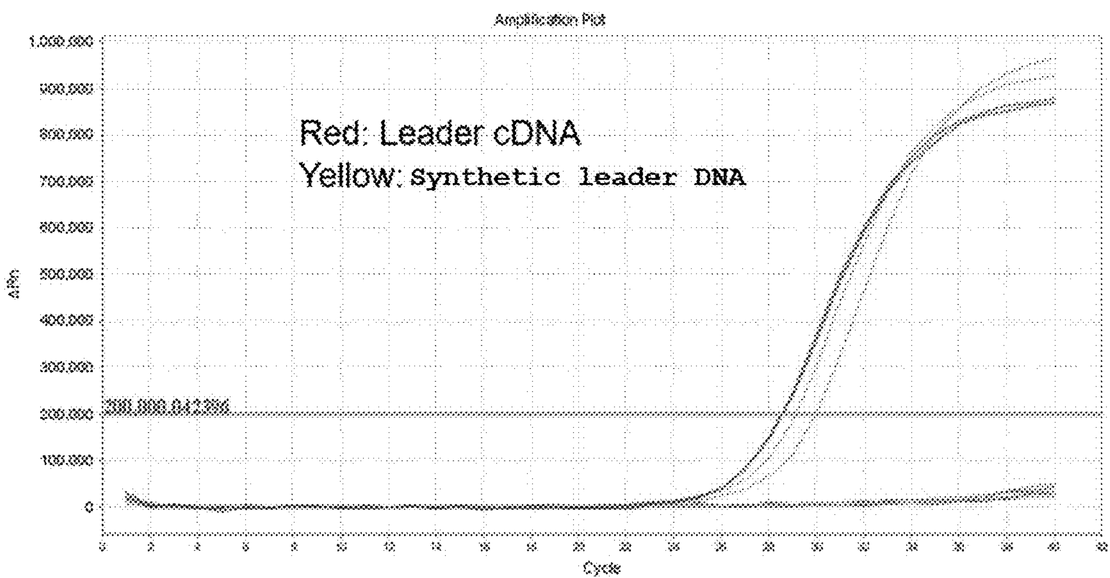
【Fig. 4】
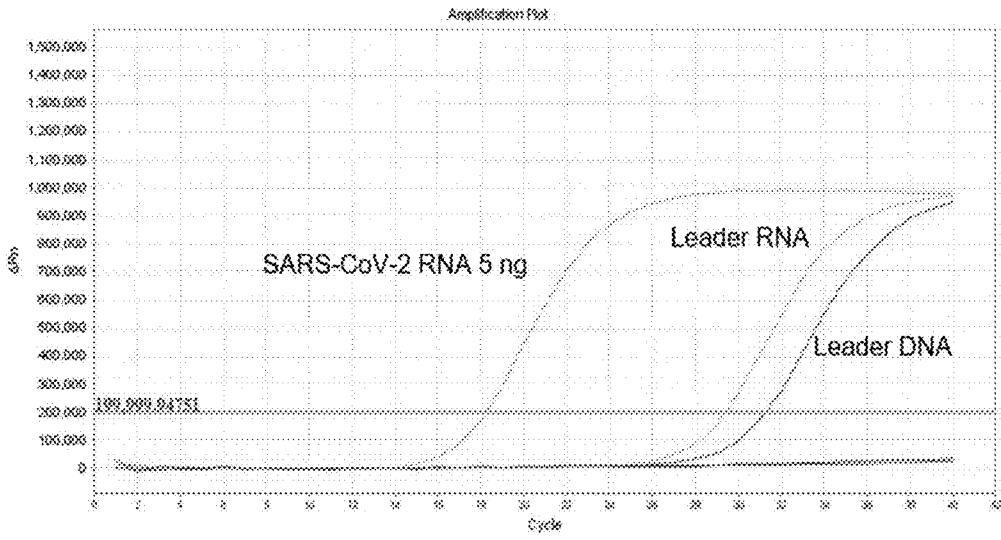

【Fig. 5a】
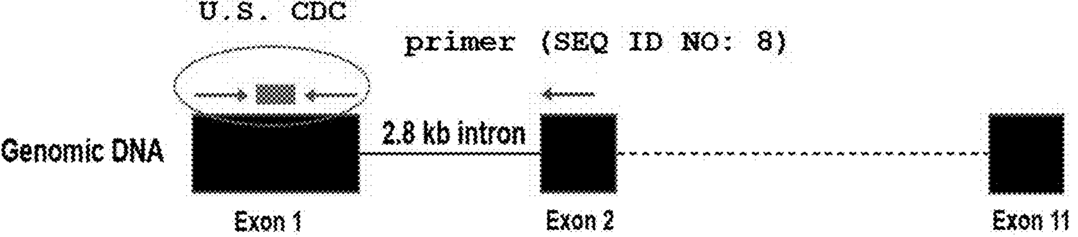
【Fig. 5b】
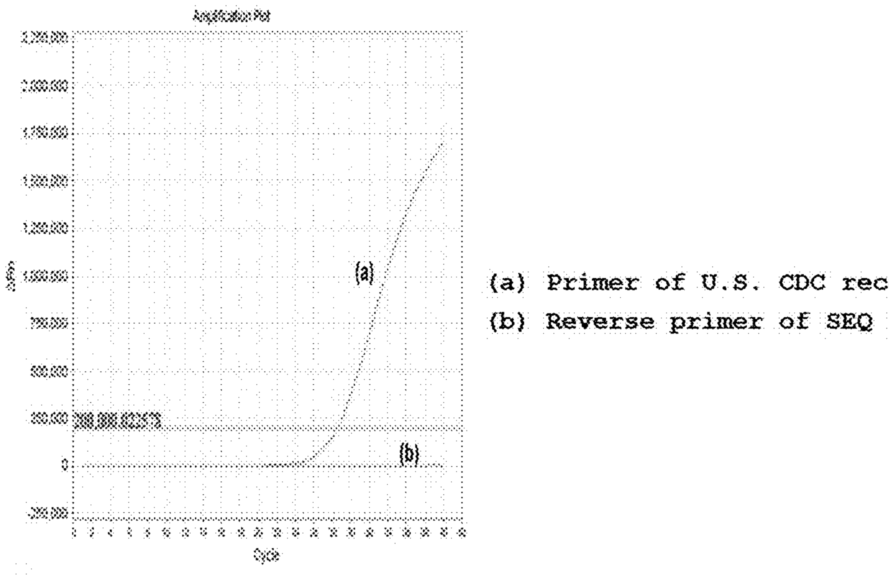

COMPOSITION FOR DIAGNOSING SARS-CoV-2, KIT, AND METHOD FOR DIAGNOSING SARS-CoV-2 BY USING SAME

CROSS-REFERENCE TO RELATED APPLICATIONS

This is a U.S. national phase under the provisions of 35 U.S.C. § 371 of International Patent Application No. PCT/KR2021/002735 filed Mar. 5, 2021, which in turn claims priority under 35 U.S.C. § 119 of Korean Patent Application No. 10-2020-0028155 filed Mar. 6, 2020. The disclosures of such applications are hereby incorporated herein by reference in their respective entireties, for all purposes.

REFERENCE TO SEQUENCE LISTING SUBMITTED VIA EFS-WEB

This application includes an electronically submitted sequence listing in .txt format. The .txt file contains a sequence listing entitled "646_SeqListing_ST25.txt" created on Jul. 19, 2022 and is 48,647 bytes in size. The sequence listing contained in this .txt file is part of the specification and is hereby incorporated by reference herein in its entirety.

TECHNICAL FIELD

The present invention relates to a composition for diagnosing infection with novel coronavirus (SARS-CoV-2: severe acute respiratory syndrome coronavirus 2), a kit including the composition, and a method of diagnosing infection with novel coronavirus using the same. More particularly, the present invention relates to a composition for diagnosing infection with novel coronavirus including a nucleic acid oligomer capable of specifically amplifying, as a target, a leader sequence present with the greatest abundance in cells infected with novel coronavirus, a kit including the composition, and a method of diagnosing infection with novel coronavirus using the same.

BACKGROUND ART

Coronavirus is a virus having a positive-sense single-stranded RNA genome about 27-32 kb long, and affects humans and other mammals. Coronavirus is known to produce genomic RNA and 6-8 subgenomic RNAs having mRNA in common at the 3' end through replication and transcription (Imbert I. et al.; A second, non-canonical RNA-dependent RNA polymerase in SARS Coronavirus. The EMBO Journal. 2006, 25:4933-4942).

Coronavirus infection in most people exhibits mild symptoms but is highly contagious, and 10,000 or more people over the past 20 years have been infected with SARS coronavirus (severe acute respiratory syndrome, having a fatality rate of 10%) and MERS coronavirus (middle east respiratory syndrome, having a fatality rate of 37%) (Chaolin Huang, Yeming Wang, Xingwang Li, Lili Ren, Jianping Zhao, Yi Hu et al.; Clinical features of patients infected with 2019 novel coronavirus in Wuhan, China. Lancet 2020).

However, the recently discovered novel coronavirus (SARS-CoV-2) infection is an acute respiratory syndrome discovered in China on December 1, 2019 (Chaolin Huang, Yeming Wang, Xingwang Li, Lili Ren, Jianping Zhao, Yi Hu et al.; Clinical features of patients infected with 2019 novel coronavirus in Wuhan, China. Lancet 2020) and first reported on Dec. 12, 2019, and shows symptoms such as fever, cough, shortness of breath, atypical pneumonia and the like.

Since January 2020, coronavirus has spread widely outside of China, and is becoming a situation of increasing concern due to, for example the rapid increase in the number of infected persons and paralysis of all urban functions in Wuhan due to rapid contagion around the Lunar New Year holiday in China.

In general, viral genomes are analyzed using methods such as SSP-PCR (single specific primer-polymerase chain reaction), real-time PCR, PCR-RFLP (PCR-restriction fragment length polymorphism analysis), and sequencing. For diagnosis of SARS-CoV-2 infection, coronavirus is first detected through a pan-coronavirus test and then a method combining real-time PCR and sequencing is used, which is problematic in that it takes 24 hours or more to diagnose the infection.

Recently, the U.S. Centers for Disease Control and Prevention (CDC) and the WHO developed and supplied RT real-time PCR (reverse transcription real-time PCR) tests to shorten the test time (Real-time RT-PCR Panel for detection 2019-Novel Coronavirus. Centers for Disease Control and Prevention, Respiratory Viruses Branch, Division of Viral Diseases). The test method developed by the U.S. Centers for Disease Control and Prevention is a method of amplifying three regions of the N gene, which codes for the nucleocapsid protein of SARS-CoV-2. The method developed by the WHO is one-step real-time PCR capable of screening and confirmation at the same time, is used for screening the E gene region, having high sequence homology with existing SARS-related viruses, and is able to amplify the RdRP (RNA-dependent RNA polymerase) gene capable of specifically detecting SARS-CoV-2 in order to confirm SARS-CoV-2 infection (FIG. 1).

However, since the E gene and the RdRP gene have low abundance in virus-infected cells, there may be cases in which detection is impossible due to experimental error or depending on RNA stability of the sample.

In addition, the U.S. Centers for Disease Control and Prevention and the WHO used the human RNase P gene as an internal control gene for determining RNA sample suitability, and disclosed primer and probe sequences for amplifying RNase P cDNA. However, the inventors of the present application ascertained that the disclosed primer and probe sequences are primers that target the inside of the first exon without considering RNA splicing, and thus false-positive amplification may occur when applied to genomic DNA. When RNA is extracted from a sample at a test site, genomic DNA is often not completely removed, so errors may occur in the determination of sample suitability.

Against this technical background, the inventors of the present application developed a new detection method targeting the leader sequence that is most abundant in initially infected cells for diagnosis of SARS-CoV-2 infection. In addition, primers for the internal control RNase P gene were constructed in consideration of RNA splicing so as to prevent false-positive amplification of genomic DNA from occurring.

The information described in this background section is only for improving understanding of the background of the present invention, and it is not to be construed as including information forming the related art already known to those of ordinary skill in the art to which the present invention belongs.

DISCLOSURE

It is an object of the present invention to address the problems encountered in the related art and to provide a composition capable of diagnosing SARS-CoV-2 infection accurately and without generating false positives, a kit, and a diagnosis method using the same.

In order to accomplish the above object, the present invention provides a composition for diagnosing coronavirus including a nucleic acid oligomer capable of specifically amplifying a coronavirus (SARS-CoV-2: severe acute respiratory syndrome coronavirus 2) leader including the sequence of SEQ ID NO: 10.

In addition, the present invention provides a kit for diagnosing coronavirus including the composition.

In addition, the present invention provides a method of providing information on coronavirus diagnosis including treating a sample with a nucleic acid oligomer capable of specifically amplifying a coronavirus (SARS-CoV-2: severe acute respiratory syndrome coronavirus 2) leader including the sequence of SEQ ID NO: 10.

DESCRIPTION OF DRAWINGS

FIG. 1 shows genes for diagnosing novel coronavirus according to WHO recommendations, and contains the following nucleotide sequences: gtgaaatggtcatgtgtggcgg (SEQ ID NO: 15); ccaggtggaacctcatcaggagatgc (SEQ ID NO: 16); tatgctaatagtgtttttaacatttg (SEQ ID NO: 17); acaggtacgttaatagttaatagcgt (SEQ ID NO: 18); acactagccatccttactgcgcttcgattgtgtgcgtactgctgcaatat (SEQ ID NO: 19);

FIG. 2 shows the mechanism by which coronavirus subgenomic RNA is expressed;

FIG. 3 shows the results of detection of the SARS-CoV-2 leader RNA sequence through RT-qPCR according to an embodiment of the present invention;

FIG. 4 shows the results of amplification of the leader sequence from SARS-CoV-2 RNA through RT-qPCR according to an embodiment of the present invention;

FIG. **5*a* shows the structure of the RNase P gene and the region that is amplified by the nucleic acid oligomer of the present invention; and FIG. 5*b*** shows the results of amplification of the RNase P gene through RT-qPCR.

MODE FOR INVENTION

Unless otherwise defined, all technical and scientific terms used herein have the same meanings as those typically understood by those skilled in the art to which the present invention belongs. In general, the nomenclature used herein is well known in the art and is typical.

The inventors of the present application confirmed that novel coronavirus infection can be quickly and accurately diagnosed through a new detection method targeting the leader sequence present with the greatest abundance in initially infected cells for diagnosis of SARS-CoV-2 infection.

An aspect of the present invention pertains to a composition for diagnosing coronavirus including a nucleic acid oligomer capable of specifically amplifying a coronavirus (SARS-CoV-2: severe acute respiratory syndrome coronavirus 2) leader including the sequence of SEQ ID NO: 10.

In addition, the present invention pertains to a method of providing information on coronavirus diagnosis including treating a sample with a nucleic acid oligomer capable of specifically amplifying a coronavirus (SARS-CoV-2: severe acute respiratory syndrome coronavirus 2) leader including the sequence of SEQ ID NO: 10.

With regard to the leader sequence, genomic RNA and transcriptionally expressed subgenomic mRNAs in coronavirus have a leader sequence of about 72-77 bp in common at the 5' end, which is a unique feature of coronavirus. Among viral sequences, the leader sequence is the target that is present with the greatest abundance in infected cells. This is because all subgenomic RNAs of coronavirus exhibit a leader-joining phenomenon by which the leader sequence (leader RNA), corresponding to about 72 bp derived from the 5' end of genomic RNA, binds to the 5' end of each subgenomic RNA.

Thus, the leader sequence has the highest number of copies among viral genes in the cell, followed by the number of copies of subgenomic RNA encoding the N protein. Therefore, the use of the leader sequence as a detection target is regarded as very effective for detection of coronavirus present in a small amount in an early stage of infection with mild symptoms.

In the present specification, the nucleic acid oligomer may be a material including two or more nucleotides produced by polymerization of nucleic acids as monomers. The nucleic acid oligomer may function as a primer or a probe.

As used herein, the term "primer" refers to a single-stranded oligonucleotide capable of initiating template-directed DNA synthesis under appropriate conditions (i.e. four different nucleoside triphosphates and a polymerase) at a suitable temperature in a buffer solution. The primer may be constructed to be "substantially" complementary with each strand of the gene locus to be amplified. This means that the primer has sufficient complementarity for hybridization with the corresponding nucleic acid strand under conditions for performing the polymerization reaction.

In one embodiment, the nucleic acid oligomer capable of specifically amplifying a coronavirus (SARS-CoV-2) leader including the sequence of SEQ ID NO: 10 may be a primer including, for example, the sequence of SEQ ID NO: 1 or SEQ ID NO: 2.

For the primer, for example, forward and reverse primers may be paired and simultaneously used for PCR. The forward primer that specifically amplifies the SARS-CoV-2 leader sequence including the sequence of SEQ ID NO: 10 may include, for example, the sequence of SEQ ID NO: 1. The reverse primer may include, for example, the sequence of SEQ ID NO: 2.

Moreover, it was confirmed that false-positive amplification of genomic DNA was prevented from occurring by constructing a primer for the internal control RNase P gene in consideration of RNA splicing.

The internal control gene is an oligonucleotide for determining RNA sample suitability, and may not be complementary with a target gene. In a specific embodiment of the present invention, the human RNase P gene was used as a conventional internal control gene.

It was confirmed that the primer and probe sequences for amplifying RNase P cDNA published by the CDC are primers that target the inside of the first exon without considering RNA splicing, and thus false-positive amplification may occur when applied to genomic DNA. When RNA is extracted from a sample at the test site, genomic DNA is often not completely removed, so errors may occur in the determination of sample suitability.

In one embodiment, a nucleic acid oligomer capable of specifically amplifying RNase P including the sequence of SEQ ID NO: 11 may be further included.

The nucleic acid oligomer may be, for example, a primer including the sequence of SEQ ID NO: 7 or SEQ ID NO: 9. It has been confirmed that the primer according to the present invention targets a sequence complementary to the 5' region of the second exon and thus false-positive amplification does not occur when applied to genomic DNA.

For the primer, for example, forward and reverse primers may be paired and simultaneously used for PCR. The forward primer specifically amplifying RNase P including the sequence of SEQ ID NO: 11 may include, for example, the sequence of SEQ ID NO: 7. The reverse primer may include, for example, the sequence of SEQ ID NO: 8.

In the present invention, a probe capable of complementary hybridization with the coronavirus leader or RNase P product that is specifically amplified by the nucleic acid oligomer may be further included.

With regard to the probe, it may be an oligonucleotide capable of hybridizing with an amplification product under specific conditions.

In a hybridization reaction, the conditions used to achieve a certain level of stringency vary depending on the properties of the nucleic acid to be hybridized. For example, the length of the nucleic acid region to be hybridized, the extent of homology, the nucleotide sequence composition (e.g. GC/AT composition ratio), and the nucleic acid type (e.g. RNA or DNA) are considered in selecting the hybridization conditions. A further consideration is whether the nucleic acid is immobilized, for example on a filter or the like.

Examples of varying stringent conditions are as follows: 2×SSC/0.1% SDS at room temperature (hybridization conditions), 0.2×SSC/0.1% SDS at room temperature (low-stringency conditions), 0.2×SSC/0.1% SDS at 42° C. (moderate-stringency conditions), and 0.1×SSC at 68° C. (high-stringency conditions). The washing process may be performed using any one of these conditions, for example high-stringency conditions, or individual conditions may be used in the order described above for 10 to 15 minutes each, and some or all of the conditions described above may be repeated. However, as described above, the optimal conditions vary depending on the specific hybridization reaction, and may be determined through experimentation. Generally, high-stringency conditions are used for hybridization of an important probe.

In one embodiment, the probe capable of complementary hybridization with the amplified coronavirus leader may include, for example, the sequence of SEQ ID NO: 3.

In one embodiment, the probe capable of complementary hybridization with the amplified RNase P product used as the internal control may include the sequence of SEQ ID NO: 9.

In some cases, the probe is detectably labeled, and may be labeled with, for example, a radioactive isotope, a fluorescent compound, a bioluminescent compound, a chemiluminescent compound, a metal chelate, or an enzyme. Appropriate labeling of the probe as described above is a technique that is well known in the art, and may be performed through a typical method.

The amount of the amplification product may be detected using a fluorescence signal. An intercalation method using an intercalator that exhibits fluorescence when bound to double-stranded DNA of the amplification product to which the probe is bound, a method using an oligonucleotide in which the 5' end is labeled with a fluorescent material and the 3' end is labeled with a quencher, and the like may be performed.

The amplification according to the present invention may be performed through real-time quantitative amplification using reverse transcriptase, for example, real-time polymerase chain reaction (real-time PCR), and the amount of the PCR amplification product in a real-time polymerase chain reaction may be detected using a fluorescence signal. During the real-time polymerase chain reaction, the intensity of the fluorescence signal increases with an increase in the amount of polynucleotide, and an amplification profile curve showing the intensity of the fluorescence signal depending on the number of amplification cycles is obtained.

In general, the amplification profile curve includes a baseline region, in which a background fluorescence signal that does not reflect the actual amount of polynucleotide appears, an exponential region, in which a fluorescence signal increases with an increase in the amount of the polynucleotide product, and a plateau region, in which there is no increase in the intensity of the fluorescence signal when the PCR reaction reaches saturation.

Typically, the fluorescence signal intensity at the transition point from the baseline region to the exponential region, particularly when the amount of the PCR amplification product reaches an amount detectable by fluorescence, is called a threshold, and the number of amplification cycles corresponding to the threshold value in the amplification profile curve is called a threshold cycle (Ct) value.

The concentration of the amplified gene may be confirmed by measuring the Ct value and analyzing the standard curve in which the concentration is determined based on the Ct (threshold cycle) value for the standard material, so methylation specific sensitivity and/or specificity may be determined.

In one embodiment, the sample may include a wide range of all biological fluids obtained from body fluids, cell lines, tissue cultures, etc. derived from a suspected patient or a subject to be diagnosed, and examples thereof may include, but are not limited to, sputum in the lower respiratory tract, oropharyngeal swab and/or nasopharyngeal swab of the upper respiratory tract, a culture sample, a tissue sample, blood, and the like.

Extracting the nucleic acid from the sample may be further included, and extraction of the nucleic acid may be performed using, for example, any of a variety of commercially available kits or extraction reagents.

Another aspect of the present invention pertains to a kit including the composition.

In one embodiment, the kit may include a compartmentalized carrier means accommodating a sample, a container including a reagent, and a container including a nucleic acid oligomer. In some cases, it may further include a container including a probe for detecting each of the gene amplification products.

The carrier means is suitable for accommodating one or more containers, such as bottles and tubes, and each container contains independent components for use in the method of the present invention. In the context of the present invention, the agent necessary for the container may be easily dispensed by those skilled in the art.

The kit according to the present invention may optionally include a reagent necessary to conduct a nucleic acid amplification PCR reaction, such as a polymerase, a buffer, and deoxyribonucleotide-5-triphosphate. The kit according to the present invention may further include various polynucleotide molecules, buffers, and reagents.

In the kit, the optimal amount of the reagent, buffer, or reactant used for a specific reaction may be determined by those skilled in the art, and the kit may be manufactured as a separate package or compartment containing each of the primers or probes described above.

EXAMPLES

A better understanding of the present invention may be obtained through the following examples. These examples are merely set forth to illustrate the present invention, and are not to be construed as limiting the scope of the present invention, as will be apparent to those skilled in the art.

Example 1: Design of Primers and Probes for Detection of SARS-CoV-2 and Internal Control Gene Primers and probes for amplification of the leader sequence cDNA (SEQ ID NO: 10) of SARS-CoV-2 (GenBank No. MN988668.1: SEQ ID NO: 12) and also the internal control gene RNase P (SEQ ID NO: 11) were designed using a Primer 3 program (http://bioinfo.ut.ee/primer3-0.4.0/) (Table 1).

TABLE 1

Primer and probe sequences

| Name | | Sequence (5' >3' ) | SEQ ID NO: | Amplification product size |
|---|---|---|---|---|
| Leader | Forward primer | ATTA AAC GTT TAT ACC TTC CCA GG | 1 | 72 |
| | Reverse primer | CGT TTA GAG AAC AGA TCT ACA AG | 2 | |
| | Probe | FAM-TAA CAA ACC AAC CAA C TTT CGA TCT-BHQ1 | 3 | |
| RNase P (U.S. CDC recom-mendation) | Forward primer | AGA TTT GGA CCT GCG AGC G | 4 | 65 |
| | Reverse primer | GAG CGG CTG TCT CCA CAA GT | 5 | |
| | Probe | TTC TGA CCT GAA GGC TCT GCG CG | 6 | |
| RNase P | Forward primer | AGA TTT GGA CCT GCG AGC G | 7 | 92 |
| | Reverse primer | TGA TAG CAA CAA CTG AAT AGC | 8 | |
| | Probe | FAM-TTC TGA CCT GAA GGC TCT GCG CG-BHQ1 | 9 | |
| Leader sequence | | ATTAAAGGTT TATACCTTCC CAGGTAACAA ACCAACCAAC TTTCGATCTC TTGTAGATCT GTTCTCTAAA CG | 10 | |
| RNase P sequence | | TGTTTGCAGA TTTGGACCTG CGAGCGGGTT CTGACCTGAA GGCTCTGCGC GGACTTGTGG AGACAGCCGC TCACCTTGGC TATTCAGTTG TTGCTATCAA TCATATCGTT GACTTTAAGG AAAAGAAACA GGAAATTGAA AAACCAGTAG CTGTTTCTGA ACTCTTCACA ACTTTGCCAA TTGTACAGGG AAAATCAAGA | 11 | |

Example 2: Synthesis of SARS-CoV-2 Leader and RNase P Gene RNA

In order to synthesize RNA corresponding to the leader sequence of SARS-CoV-2, DNA corresponding to 110 bp (SEQ ID NO: 13) including the leader sequence 72 bp long (SEQ ID NO: 10) of SARS-CoV-2 was synthesized (Neo-Probe, Korea). In order to synthesize RNA of the RNase P gene (GenBank No. NC_000010.11: SEQ ID NO: 14), 180-bp DNA (SEQ ID NO: 2) corresponding to the RNase P sequence was synthesized. RNA was constructed through an in-vitro transcription method by linking the T7 promoter sequence to the 5' end of each synthesized DNA.

(1) In-Vitro Transcription (IVT)

50 ng of each of the two template PCR products was allowed to react as follows using a MEGAScript™ T7 Transcription kit (Invitrogen) according to the manufacturer's instructions.

TABLE 2

| Ingredient | Amount used | Reaction conditions |
|---|---|---|
| Leader, RNase P PCR product | 50 ng | At 37° C. for 2 hours |
| ATP (10 mM) | 2 μl | |
| GTP (10 mM) | 2 μl | |
| CTP (10 mM) | 2 μl | |
| UTP (10 mM) | 2 μl | |
| 10X Buffer | 2 μl | |

TABLE 2-continued

| Ingredient | Amount used | Reaction conditions |
|---|---|---|
| T7 Enzyme | 2 μl | |
| Total volume | 20 μl | |

After reaction for 2 hours, 4 μl of DNase was added to remove remaining DNA and allowed to react at 37° C. for 15 minutes. The synthesized leader and RNase P RNA were purified using a QIAamp RNeasy Mini kit (Qiagen) according to the manufacturer's instructions. Finally, the synthesized RNA was eluted with 50 μl of RNase-free DW.

Example 3: Detection of Reverse Transcription Polymerase Real-Time SARS-CoV-2 Leader cDNA and RNase P cDNA RT-qPCR was performed as follows. The reaction solution composition is shown in the following table, and an AB 7500 Fast (ThermoFisher, USA) system was used for the RT-qPCR reaction. In the first reverse transcription (RT) step, cDNA complementary to RNA was synthesized, and in the second real-time PCR (qPCR) step, cDNA was amplified.

TABLE 3

| RT-qPCR reaction solution composition | | |
|---|---|---|
| Reagent | Concentration | Volume (uL) |
| RNA sample | — | 5 |
| Master mix* | 4X | 5 |
| Forward primer | 10 pmole/uL | 1 |
| Reverse primer | 10 pmole/uL | 1 |
| Probe | 5 pmole/uL | 1 |
| RNase free water | — | 8 |
| Total | — | 20 |

*TOPreal One-step RT-qPCR kit (Enzynomics, Korea)

TABLE 4

| RT-qPCR conditions | | | | |
|---|---|---|---|---|
| Step | Stage | Cycles | Temperature | Time |
| Reverse transcription | 1 | 1 | 50° C. | 30 min |
| RT-Inactivation/ Initial denaturation | 2 | 1 | 95° C. | 10 min |
| Amplification | 3 | 40 | 95° C.<br>60° C. | 15 sec<br>60 sec |

(1) Results of Detection of SARS-CoV-2 Leader RNA Sequence

In order to confirm detection of cDNA complementary to the SARS-CoV-2 leader RNA sequence, one-step RT-qPCR was performed using leader RNA (104 copies), leader DNA (104 copies) used for in-vitro transcription, human genomic DNA (10 ng), and human total RNA (10 ng) (FIG. 3). Consequently, amplification was confirmed only in the leader cDNA and leader DNA, and it was confirmed that there was no nonspecific amplification in the remaining templates (Table 5).

TABLE 5

| Results of detection of SARS-CoV-2 leader RNA | |
|---|---|
| Sample | Amplification factor (Cycle Threshold: $C_T$) |
| Leader RNA ($10^4$ copies) | 28.6<br>28.5 |
| Leader DNA ($10^4$ copies) | 30.0<br>29.1 |
| Human genomic DNA (10 ng) | Not detected<br>Not detected |
| Human total RNA (10 ng) | Not detected<br>Not detected |
| D.W | Not detected<br>Not detected |

In order to determine amplification of the SARS-CoV-2 leader RNA in practice, RNA isolated by culturing SARS-CoV-2 isolated from Koreans at the National Culture Collection for Pathogens in Korea was used. One-step RT-qPCR was performed in the same manner as above. Based on the test results, it was confirmed that the leader RNA of SARS-CoV-2 was normally amplified (FIG. 4 and Table 6).

TABLE 6

| Results of detection of leader RNA from SARS-CoV-2 RNA | |
|---|---|
| Sample | Amplification factor (Cycle Threshold: $C_T$) |
| SARS-CoV-2 RNA (5 ng) | 18.2 |
| Leader RNA ($10^4$ copies) | 29.4 |
| Leader DNA | 31.3 |
| D.W | Not detected |

(2) Results of Detection of RNase P RNA

Human RNase P gene was used as an internal control gene for determining RNA sample suitability. For primers and probes for amplifying RNase P RNA, although there were sequences disclosed by the U.S. Centers for Disease Control and Prevention, based on the results of confirmation by the inventors of the present application, the primers were constructed inside the first exon without considering RNA splicing, so false-positive amplification of genomic DNA occurred.

Because genomic DNA is often not completely removed when RNA is extracted from a sample, errors may occur in determining sample suitability. Hence, in order to solve this problem, the present inventors constructed a novel reverse primer in consideration of RNA splicing so as to prevent false-positive amplification of genomic DNA from occurring.

As shown in FIG. 5*a*, the RNase P gene is a gene composed of a total sequence of about 36.6 kb, and consists of a total of 11 exons.

All of the primers and probes corresponding to the RNase P gene sequence provided by the U.S. Centers for Disease Control and Prevention were constructed at the region corresponding to the first exon without considering RNA splicing, and when amplifying human genomic DNA, false-positive amplification occurred ((a) in FIG. 5*b*). In contrast, when the reverse primer developed by the present inventors was used, false-positive amplification of human genomic DNA did not occur ((b) in FIG. 5*b*).

Therefore, the present inventors solved the problem of false-positive amplification by genomic DNA by newly constructing a reverse primer for a region complementary to the 5' region of the second exon about 2.8 kb away. Based on the results of amplification of IVT-generated RNase P RNA and human total RNA, it was confirmed that normal amplification occurred (Table 7).

TABLE 7

| RNase P gene amplification results | |
|---|---|
| Sample | Amplification factor (Cycle Threshold: $C_T$) |
| RNase P RNA (10 pg) | 14.5 |
| Human total RNA (10 ng) | 26.6 |
| D.W | Not detected |

Example 4: Evaluation of Ability to Diagnose SARS-CoV-2 Using Leader Sequence In order to evaluate the ability to diagnose SARS-CoV-2 using the leader sequence of SEQ ID NO: 10, RNA was extracted from upper respiratory tract samples for which the SARS-CoV-2 diagnosis result is already known (180 negatives, 76 positives) stored at Yeungnam University Medical Center (IRB No. YUMC 2020-07-001) using a QIAamp Viral RNA Mini kit (Qiagen, Cat. No: 52904 or 52906) according to the manufacturer's protocol. The RNase P gene was used as an internal control (IC CT values in Table 8).

In order to diagnose SARS-CoV-2 infection, RT-qPCR was performed through the method described in Example 3 (Table 8).

TABLE 8

SARS-CoV-2 RT-qPCR results using leader sequence

| Registration number | Diagnosis result | Diagnosis result using leader sequence | | |
|---|---|---|---|---|
| | | Leader CT | IC CT | Diagnosis result |
| R001 | Negative | ND | 26.6 | Negative |
| R002 | Negative | ND | 28.38 | Negative |
| R003 | Negative | ND | 24.29 | Negative |
| R004 | Negative | ND | 25.91 | Negative |
| R005 | Negative | ND | 25.87 | Negative |
| R006 | Negative | ND | 23.5 | Negative |
| R007 | Negative | ND | 26.93 | Negative |
| R008 | Negative | ND | 25.21 | Negative |
| R009 | Negative | ND | 25.94 | Negative |
| R010 | Negative | ND | 27.27 | Negative |
| R011 | Negative | ND | 26 | Negative |
| R012 | Negative | ND | 28.51 | Negative |
| R013 | Negative | ND | 24.01 | Negative |
| R014 | Negative | ND | 23.96 | Negative |
| R015 | Negative | ND | 28.24 | Negative |
| R016 | Negative | ND | 27.07 | Negative |
| R017 | Negative | ND | 25.33 | Negative |
| R018 | Negative | ND | 26.9 | Negative |
| R019 | Negative | ND | 25.13 | Negative |
| R020 | Negative | ND | 26.34 | Negative |
| R021 | Negative | ND | 27.14 | Negative |
| R022 | Negative | ND | 27.48 | Negative |
| R023 | Negative | ND | 25.6 | Negative |
| R024 | Negative | ND | 25.65 | Negative |
| R025 | Negative | ND | 25.59 | Negative |
| R026 | Negative | ND | 27.62 | Negative |
| R027 | Negative | ND | 29 | Negative |
| R028 | Negative | ND | 24.87 | Negative |
| R029 | Negative | ND | 27.73 | Negative |
| R030 | Negative | ND | 27.02 | Negative |
| R031 | Negative | ND | 26.83 | Negative |
| R032 | Negative | ND | 25.82 | Negative |
| R033 | Negative | ND | 26.37 | Negative |
| R034 | Negative | ND | 27.66 | Negative |
| R035 | Negative | ND | 27.17 | Negative |
| R036 | Negative | ND | 25.01 | Negative |
| R037 | Negative | ND | 23.79 | Negative |
| R038 | Negative | ND | 29.59 | Negative |
| R039 | Negative | ND | 24.02 | Negative |
| R040 | Negative | ND | 28.06 | Negative |
| R041 | Negative | ND | 24.95 | Negative |
| R042 | Negative | ND | 24.04 | Negative |
| R043 | Negative | ND | 26.61 | Negative |
| R044 | Negative | ND | 25.9 | Negative |
| R045 | Negative | ND | 25.08 | Negative |
| R046 | Negative | ND | 23.81 | Negative |
| R047 | Negative | ND | 24.37 | Negative |
| R048 | Negative | ND | 24.17 | Negative |
| R049 | Negative | ND | 29.86 | Negative |
| R050 | Negative | ND | 26.25 | Negative |
| R051 | Negative | ND | 27.9 | Negative |
| R052 | Negative | ND | 27.35 | Negative |
| R053 | Negative | ND | 25.89 | Negative |
| R054 | Negative | ND | 27.4 | Negative |
| R055 | Negative | ND | 24.25 | Negative |
| R056 | Negative | ND | 27.25 | Negative |
| R057 | Negative | ND | 25.26 | Negative |
| R058 | Negative | ND | 24.2 | Negative |
| R059 | Negative | ND | 28.34 | Negative |
| R060 | Negative | ND | 26.49 | Negative |
| R061 | Negative | ND | 22.59 | Negative |
| R062 | Negative | ND | 24.98 | Negative |
| R063 | Negative | ND | 25.13 | Negative |
| R064 | Negative | ND | 25.73 | Negative |
| R065 | Negative | ND | 29.11 | Negative |
| R066 | Negative | ND | 27.97 | Negative |
| R067 | Negative | ND | 25.16 | Negative |
| R068 | Negative | ND | 26.24 | Negative |
| R069 | Negative | ND | 25.03 | Negative |

TABLE 8-continued

SARS-CoV-2 RT-qPCR results using leader sequence

| Registration number | Diagnosis result | Diagnosis result using leader sequence | | |
|---|---|---|---|---|
| | | Leader CT | IC CT | Diagnosis result |
| R070 | Negative | ND | 25.79 | Negative |
| R071 | Negative | ND | 23.83 | Negative |
| R072 | Negative | ND | 24.51 | Negative |
| R073 | Negative | ND | 25.32 | Negative |
| R074 | Negative | ND | 24.65 | Negative |
| R075 | Negative | ND | 29.24 | Negative |
| R076 | Negative | ND | 22.25 | Negative |
| R077 | Negative | ND | 23.34 | Negative |
| R078 | Negative | ND | 24.36 | Negative |
| R079 | Negative | ND | 22.93 | Negative |
| R080 | Negative | ND | 20.96 | Negative |
| R081 | Negative | ND | 25.95 | Negative |
| R082 | Negative | ND | 28.71 | Negative |
| R083 | Negative | ND | 25.68 | Negative |
| R084 | Negative | ND | 28.28 | Negative |
| R085 | Negative | ND | 27.91 | Negative |
| R086 | Negative | ND | 27.89 | Negative |
| R087 | Negative | ND | 30.47 | Negative |
| R088 | Negative | ND | 26.24 | Negative |
| R089 | Negative | ND | 27.64 | Negative |
| R090 | Negative | ND | 26.04 | Negative |
| R091 | Negative | ND | 26.55 | Negative |
| R092 | Negative | ND | 27.4 | Negative |
| R093 | Negative | ND | 26.83 | Negative |
| R094 | Negative | ND | 28.07 | Negative |
| R095 | Negative | ND | 25.92 | Negative |
| R096 | Negative | ND | 22.33 | Negative |
| R097 | Negative | ND | 26.18 | Negative |
| R098 | Negative | ND | 26.38 | Negative |
| R099 | Negative | ND | 27.58 | Negative |
| R100 | Negative | ND | 26.81 | Negative |
| R101 | Negative | ND | 24.08 | Negative |
| R102 | Negative | ND | 27.34 | Negative |
| R103 | Negative | ND | 27.97 | Negative |
| R104 | Negative | ND | 26.03 | Negative |
| R105 | Negative | ND | 28.27 | Negative |
| R106 | Negative | ND | 25.36 | Negative |
| R107 | Negative | ND | 24.23 | Negative |
| R108 | Negative | ND | 27.33 | Negative |
| R109 | Negative | ND | 25.48 | Negative |
| R110 | Negative | ND | 28.53 | Negative |
| R111 | Negative | ND | 24.97 | Negative |
| R112 | Negative | ND | 28.09 | Negative |
| R113 | Negative | ND | 24.64 | Negative |
| R114 | Negative | ND | 24.02 | Negative |
| R115 | Negative | ND | 24.97 | Negative |
| R116 | Negative | ND | 25.91 | Negative |
| R117 | Negative | ND | 22.33 | Negative |
| R118 | Negative | ND | 25.56 | Negative |
| R119 | Negative | ND | 23.95 | Negative |
| R120 | Negative | ND | 25.59 | Negative |
| R121 | Negative | ND | 24.63 | Negative |
| R122 | Negative | ND | 25.28 | Negative |
| R123 | Negative | ND | 24.96 | Negative |
| R124 | Negative | ND | 21.72 | Negative |
| R125 | Negative | ND | 23.01 | Negative |
| R126 | Negative | ND | 23.88 | Negative |
| R127 | Negative | ND | 22.66 | Negative |
| R128 | Negative | ND | 25.04 | Negative |
| R129 | Negative | ND | 26.42 | Negative |
| R130 | Negative | ND | 25.93 | Negative |
| R131 | Negative | ND | 30.15 | Negative |
| R132 | Negative | ND | 27.59 | Negative |
| R133 | Negative | ND | 27.36 | Negative |
| R134 | Negative | ND | 24.31 | Negative |
| R135 | Negative | ND | 26.59 | Negative |
| R136 | Negative | ND | 26.55 | Negative |
| R137 | Negative | ND | 24.53 | Negative |
| R138 | Negative | ND | 24.56 | Negative |
| R139 | Negative | ND | 25.42 | Negative |
| R140 | Negative | ND | 24.22 | Negative |
| R141 | Negative | ND | 24.7 | Negative |
| R142 | Negative | ND | 27.19 | Negative |
| R143 | Negative | ND | 24.59 | Negative |

TABLE 8-continued

SARS-CoV-2 RT-qPCR results using leader sequence

| Registration number | Diagnosis result | Diagnosis result using leader sequence | | |
|---|---|---|---|---|
| | | Leader CT | IC CT | Diagnosis result |
| R144 | Negative | ND | 28.67 | Negative |
| R145 | Negative | ND | 27.58 | Negative |
| R146 | Negative | ND | 27.21 | Negative |
| R147 | Negative | ND | 27.7 | Negative |
| R148 | Negative | ND | 24.85 | Negative |
| R149 | Negative | ND | 25.44 | Negative |
| R150 | Negative | ND | 25.13 | Negative |
| R151 | Negative | ND | 28.13 | Negative |
| R152 | Negative | ND | 28.61 | Negative |
| R153 | Negative | ND | 28.67 | Negative |
| R154 | Negative | ND | 28.59 | Negative |
| R155 | Negative | ND | 27.42 | Negative |
| R156 | Negative | ND | 27.96 | Negative |
| R157 | Negative | ND | 29.43 | Negative |
| R158 | Negative | ND | 27.37 | Negative |
| R159 | Negative | ND | 25.77 | Negative |
| R160 | Negative | ND | 26.92 | Negative |
| R161 | Negative | ND | 25.88 | Negative |
| R162 | Negative | ND | 26.77 | Negative |
| R163 | Negative | ND | 26.09 | Negative |
| R164 | Negative | ND | 24.66 | Negative |
| R165 | Negative | ND | 24.1 | Negative |
| R166 | Negative | ND | 24.45 | Negative |
| R167 | Negative | ND | 30.2 | Negative |
| R168 | Negative | ND | 23.26 | Negative |
| R169 | Negative | ND | 23.81 | Negative |
| R170 | Negative | ND | 25.79 | Negative |
| R171 | Negative | ND | 27.42 | Negative |
| R172 | Negative | ND | 25.4 | Negative |
| R173 | Negative | ND | 28.27 | Negative |
| R174 | Negative | ND | 24.02 | Negative |
| R175 | Negative | ND | 26.58 | Negative |
| R176 | Negative | ND | 25.87 | Negative |
| R177 | Negative | ND | 23.54 | Negative |
| R178 | Negative | ND | 26.46 | Negative |
| R179 | Negative | ND | 27.93 | Negative |
| R180 | Negative | ND | 24.93 | Negative |
| R181 | Positive | 15.89 | 29.1 | Positive |
| R182 | Positive | 17.51 | 24.48 | Positive |
| R183 | Positive | 24.65 | 26.08 | Positive |
| R184 | Positive | 30.43 | 26.78 | Positive |
| R185 | Positive | 25.29 | 23.49 | Positive |
| R186 | Positive | 15.79 | 33.8 | Positive |
| R187 | Positive | 18.96 | 30.92 | Positive |
| R188 | Positive | 17.8 | 26.92 | Positive |
| R189 | Positive | 23.24 | 22.15 | Positive |
| R191 | Positive | 17.58 | 24.51 | Positive |
| R192 | Positive | 18.6 | 22.82 | Positive |
| R193 | Positive | 17.43 | 25.46 | Positive |
| R194 | Positive | 13.93 | 30.9 | Positive |
| R195 | Positive | 30.01 | 24.01 | Positive |
| R196 | Positive | 26.91 | 26.21 | Positive |
| R197 | Positive | 22.91 | 25.95 | Positive |
| R198 | Positive | 18.54 | 28.18 | Positive |
| R199 | Positive | 25.64 | 24.18 | Positive |
| R200 | Positive | 16.22 | 25.53 | Positive |
| R201 | Positive | 29.71 | 24.5 | Positive |
| R202 | Positive | 15.93 | 25.56 | Positive |
| R203 | Positive | 22.19 | 24.07 | Positive |
| R204 | Positive | 23.73 | 23.03 | Positive |
| R205 | Positive | 23.13 | 22.97 | Positive |
| R206 | Positive | 23.84 | 23.44 | Positive |
| R207 | Positive | 21.63 | 24.55 | Positive |
| R208 | Positive | 17.07 | 31.71 | Positive |
| R209 | Positive | 30.1 | 26.43 | Positive |
| R210 | Positive | 30.04 | 25.76 | Positive |
| R211 | Positive | 23.63 | 24.32 | Positive |
| R212 | Positive | 20.47 | 25.35 | Positive |
| R213 | Positive | 16.1 | 31.59 | Positive |
| R214 | Positive | 22.93 | 23.94 | Positive |
| R215 | Positive | 20.87 | 24.92 | Positive |
| R216 | Positive | 22.26 | 25.59 | Positive |
| R217 | Positive | 23.36 | 23.59 | Positive |
| R218 | Positive | 22.04 | 24.35 | Positive |
| R219 | Positive | 27.45 | 24.91 | Positive |
| R220 | Positive | 30.93 | 27.3 | Positive |
| R221 | Positive | 25.13 | 24.84 | Positive |
| R222 | Positive | 24.68 | 23.88 | Positive |
| R223 | Positive | 23.54 | 23.72 | Positive |
| R224 | Positive | 24.18 | 25.31 | Positive |
| R225 | Positive | 15.54 | 21.19 | Positive |
| R226 | Positive | 28.36 | 25.1 | Positive |
| R227 | Positive | 22.45 | 24.56 | Positive |
| R228 | Positive | 28.09 | 25.5 | Positive |
| R229 | Positive | 30.9 | 23.31 | Positive |
| R230 | Positive | 26.27 | 26.84 | Positive |
| R231 | Positive | 27.06 | 29.85 | Positive |
| R232 | Positive | 31.67 | 30.33 | Positive |
| R233 | Positive | 25.96 | 28.19 | Positive |
| R234 | Positive | 31.34 | 25.67 | Positive |
| R235 | Positive | 26.93 | 26.12 | Positive |
| R236 | Positive | 28.01 | 24.88 | Positive |
| R237 | Positive | 26.1 | 26.13 | Positive |
| R238 | Positive | 18.26 | 24.35 | Positive |
| R239 | Positive | 15.31 | 23.62 | Positive |
| R240 | Positive | 21.89 | 22.6 | Positive |
| R241 | Positive | 26.76 | 20.97 | Positive |
| R242 | Positive | 26.95 | 24.8 | Positive |
| R243 | Positive | 21.65 | 23.8 | Positive |
| R244 | Positive | 28.88 | 24.01 | Positive |
| R245 | Positive | 31.38 | 25.43 | Positive |
| R246 | Positive | 31.93 | 29.09 | Positive |
| R247 | Positive | 28.36 | 25.58 | Positive |
| R248 | Positive | 28.93 | 23.44 | Positive |
| R249 | Positive | 20.91 | 23.07 | Positive |
| R250 | Positive | 14.19 | ND | Positive |
| R251 | Positive | 19.31 | 23.99 | Positive |
| R252 | Positive | 20.19 | 28.99 | Positive |
| R253 | Positive | 12.24 | 36.99 | Positive |
| R254 | Positive | 22.39 | 27.87 | Positive |
| R255 | Positive | 21.85 | 24.74 | Positive |
| R256 | Positive | 23.42 | 24.13 | Positive |
| R257 | Positive | 19.99 | 23.32 | Positive |

Based on the results of diagnosis of SARS-CoV-2 using the leader sequence, it was confirmed that sensitivity was 100% (76/76) and specificity was 100% (180/180), which was regarded as excellent (Table 9). Therefore, it was confirmed that the use of the leader sequence for diagnosis of SARS-CoV-2 was effective.

TABLE 9

SARS-Co test medical device sensitivity and specificity using leader sequence

| Sensitivity (%) | Specificity (%) | Sensitivity 95% confidence interval | Specificity 95% confidence interval |
|---|---|---|---|
| 100 | 100 | 95.3-100 | 97.9-100 |

INDUSTRIAL APPLICABILITY

According to the present invention, diagnosis results can be obtained in a short time, making it possible to quickly diagnose novel coronavirus infection, and enabling accurate diagnosis by preventing false positives from occurring.

Although specific embodiments of the present invention have been disclosed in detail above, it will be obvious to those skilled in the art that the description is merely of preferable exemplary embodiments and is not to be construed as limiting the scope of the present invention. Therefore, the substantial scope of the present invention will be defined by the appended claims and equivalents thereof.

SEQUENCE LIST FREE TEXT

An electronic file is attached.

The invention claimed is:

1. A composition for detecting a severe acute respiratory syndrome coronavirus 2 (SARS-CoV-2) leader sequence consisting of the sequence of SEQ ID NO: 10, the composition comprising:

(i) a nucleic acid oligomer consisting of the sequence of SEQ ID NO: 1;

(ii) a nucleic acid oligomer consisting of the sequence of SEQ ID NO: 2; and (iii) a probe a labeled probe consisting of SEQ ID NO: 3, a fluorescent compound and a quencher;

the nucleic acid oligomers (i) and (ii) being effective to specifically amplify a portion of the severe acute respiratory syndrome coronavirus 2 (SARS-CoV-2) leader sequence consisting of the sequence of SEQ ID NO: 10, when the composition comprising the nucleic acid oligomers (i) and (ii) is contacted in a reverse transcription polymerase chain reaction with a human sample in which the severe acute respiratory syndrome coronavirus 2 (SARS-CoV-2) is present, to produce a SARS-CoV-2 leader sequence amplification product, and the probe (iii) being effective to complementarily hybridize with the SARS-CoV-2 leader sequence amplification product, to thereby detect presence or absence of SARS-CoV-2 infection in the human sample, with sensitivity and specificity of detection that avoids false-positive amplification of genomic DNA in the human sample.

2. A kit for diagnosing coronavirus comprising the composition according to claim 1.

3. A method of providing information on coronavirus diagnosis comprising treating a sample with the composition of claim 1 and amplifying a target and determining whether the SARS-CoV-2 leader sequence is present.

4. The method according to claim 3, wherein the amplifying is performed through RT-qPCR (quantitative reverse transcription PCR).

* * * * *

SEQUENCE LISTING

```
<160> NUMBER OF SEQ ID NOS: 19

<210> SEQ ID NO 1
<211> LENGTH: 24
<212> TYPE: DNA
<213> ORGANISM: Artificial Sequence
<220> FEATURE:
<223> OTHER INFORMATION: Primer

<400> SEQUENCE: 1

attaaaggtt tataccttcc cagg                                            24


<210> SEQ ID NO 2
<211> LENGTH: 23
<212> TYPE: DNA
<213> ORGANISM: Artificial Sequence
<220> FEATURE:
<223> OTHER INFORMATION: Primer

<400> SEQUENCE: 2

cgtttagaga acagatctac aag                                             23


<210> SEQ ID NO 3
<211> LENGTH: 25
<212> TYPE: DNA
<213> ORGANISM: Artificial Sequence
<220> FEATURE:
<223> OTHER INFORMATION: Probe

<400> SEQUENCE: 3

taacaaacca accaactttc gatct                                           25


<210> SEQ ID NO 4
<211> LENGTH: 19
<212> TYPE: DNA
<213> ORGANISM: Artificial Sequence
<220> FEATURE:
<223> OTHER INFORMATION: Primer

<400> SEQUENCE: 4

agatttggac ctgcgagcg                                                  19


<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5

gagcggctgt ctccacaagt                                                 20


<210> SEQ ID NO 6
<211> LENGTH: 23
<212> TYPE: DNA
<213> ORGANISM: Artificial Sequence
<220> FEATURE:
<223> OTHER INFORMATION: Probe

<400> SEQUENCE: 6
```

```
ttctgacctg aaggctctgc gcg                                    23


<210> SEQ ID NO 7
<211> LENGTH: 19
<212> TYPE: DNA
<213> ORGANISM: Artificial Sequence
<220> FEATURE:
<223> OTHER INFORMATION: Primer

<400> SEQUENCE: 7

agatttggac ctgcgagcg                                         19


<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8

tgatagcaac aactgaatag c                                      21


<210> SEQ ID NO 9
<211> LENGTH: 23
<212> TYPE: DNA
<213> ORGANISM: Artificial Sequence
<220> FEATURE:
<223> OTHER INFORMATION: Probe

<400> SEQUENCE: 9

ttctgacctg aaggctctgc gcg                                    23


<210> SEQ ID NO 10
<211> LENGTH: 72
<212> TYPE: DNA
<213> ORGANISM: Artificial Sequence
<220> FEATURE:
<223> OTHER INFORMATION: Synthetic construct

<400> SEQUENCE: 10

attaaaggtt tataccttcc caggtaacaa accaaccaac tttcgatctc ttgtagatct     60

gttctctaaa cg                                                72


<210> SEQ ID NO 11
<211> LENGTH: 200
<212> TYPE: DNA
<213> ORGANISM: Artificial Sequence
<220> FEATURE:
<223> OTHER INFORMATION: Synthetic construct

<400> SEQUENCE: 11

tgtttgcaga tttggacctg cgagcgggtt ctgacctgaa ggctctgcgc ggacttgtgg     60

agacagccgc tcaccttggc tattcagttg ttgctatcaa tcatatcgtt gactttaagg    120

aaaagaaaca ggaaattgaa aaaccagtag ctgtttctga actcttcaca actttgccaa    180

ttgtacaggg aaaatcaaga                                       200


<210> SEQ ID NO 12
<211> LENGTH: 29881
<212> TYPE: DNA
<213> ORGANISM: Artificial Sequence
<220> FEATURE:
<223> OTHER INFORMATION: SARS-COV-2 synthetic construct
```

<400> SEQUENCE: 12

```
ttaaaggttt ataccttccc aggtaacaaa ccaaccaact ttcgatctct tgtagatctg     60
ttctctaaac gaactttaaa atctgtgtgg ctgtcactcg gctgcatgct tagtgcactc    120
acgcagtata attaataact aattactgtc gttgacagga cacgagtaac tcgtctatct    180
tctgcaggct gcttacggtt tcgtccgtgt tgcagccgat catcagcaca tctaggtttc    240
gtccgggtgt gaccgaaagg taagatggag agccttgtcc ctggtttcaa cgagaaaaca    300
cacgtccaac tcagtttgcc tgttttacag gttcgcgacg tgctcgtacg tggctttgga    360
gactccgtgg aggaggtctt atcagaggca cgtcaacatc ttaaagatgg cacttgtggc    420
ttagtagaag ttgaaaaagg cgttttgcct caacttgaac agccctatgt gttcatcaaa    480
cgttcggatg ctcgaactgc acctcatggt catgttatgg ttgagctggt agcagaactc    540
gaaggcattc agtacggtcg tagtggtgag acacttggtg tccttgtccc tcatgtgggc    600
gaaataccag tggcttaccg caaggttctt cttcgtaaga acggtaataa aggagctggt    660
ggccatagtt acggcgccga tctaaagtca tttgacttag gcgacgagct tggcactgat    720
ccttatgaag attttcaaga aaactggaac actaaacata gcagtggtgt tacccgtgaa    780
ctcatgcgtg agcttaacgg aggggcatac actcgctatg tcgataacaa cttctgtggc    840
cctgatggct accctcttga gtgcattaaa gaccttctag cacgtgctgg taaagcttca    900
tgcactttgt ccgaacaact ggactttatt gacactaaga ggggtgtata ctgctgccgt    960
gaacatgagc atgaaattgc ttggtacacg gaacgttctg aaaagagcta tgaattgcag   1020
acaccttttg aaattaaatt ggcaaagaaa tttgacacct tcaatgggga atgtccaaat   1080
tttgtatttc ccttaaattc cataatcaag actattcaac caagggttga aaagaaaaag   1140
cttgatggct ttatgggtag aattcgatct gtctatccag ttgcgtcacc aaatgaatgc   1200
aaccaaatgt gcctttcaac tctcatgaag tgtgatcatt gtggtgaaac ttcatggcag   1260
acgggcgatt ttgttaaagc cacttgcgaa ttttgtggca ctgagaattt gactaaagaa   1320
ggtgccacta cttgtggtta cttaccccaa aatgctgttg ttaaaattta ttgtccagca   1380
tgtcacaatt cagaagtagg acctgagcat agtcttgccg aataccataa tgaatctggc   1440
ttgaaaacca ttcttcgtaa gggtggtcgc actattgcct ttggaggctg tgtgttctct   1500
tatgttggtt gccataacaa gtgtgcctat tgggttccac gtgctagcgc taacataggt   1560
tgtaaccata caggtgttgt tggagaaggt tccgaaggtc ttaatgacaa ccttcttgaa   1620
atactccaaa aagagaaagt caacatcaat attgttggtg actttaaact taatgaagag   1680
atcgccatta ttttggcatc tttttctgct tccacaagtg cttttgtgga aactgtgaaa   1740
ggtttggatt ataaagcatt caaacaaatt gttgaatcct gtggtaattt taaagttaca   1800
aaaggaaaag ctaaaaaagg tgcctggaat attggtgaac agaaatcaat actgagtcct   1860
ctttatgcat ttgcatcaga ggctgctcgt gttgtacgat caattttctc ccgcactctt   1920
gaaactgctc aaaattctgt gcgtgtttta cagaaggccg ctataacaat actagatgga   1980
atttcacagt attcactgag actcattgat gctatgatgt tcacatctga tttggctact   2040
aacaatctag ttgtaatggc ctacattaca ggtggtgttg ttcagttgac ttcgcagtgg   2100
ctaactaaca tctttggcac tgtttatgaa aaactcaaac ccgtccttga ttggcttgaa   2160
gagaagttta aggaaggtgt agagtttctt agagacggtt gggaaattgt taaatttatc   2220
tcaacctgtg cttgtgaaat tgtcggtgga caaattgtca cctgtgcaaa ggaaattaag   2280
gagagtgttc agacattctt taagcttgta aataaatttt tggctttgtg tgctgactct   2340
```

```
atcattattg gtggagctaa acttaaagcc ttgaatttag gtgaaacatt tgtcacgcac   2400
tcaaagggat tgtacagaaa gtgtgttaaa tccagagaag aaactggcct actcatgcct   2460
ctaaaagccc caaaagaaat tatcttctta gagggagaaa cacttcccac agaagtgtta   2520
acagaggaag ttgtcttgaa aactggtgat ttacaaccat tagaacaacc tactagtgaa   2580
gctgttgaag ctccattggt tggtacacca gtttgtatta acgggcttat gttgctcgaa   2640
atcaaagaca cagaaaagta ctgtgccctt gcacctaata tgatggtaac aaacaatacc   2700
ttcacactca aaggcggtgc accaacaaag gttacttttg gtgatgacac tgtgatagaa   2760
gtgcaaggtt acaagagtgt gaatatcact tttgaacttg atgaaaggat tgataaagta   2820
cttaatgaga agtgctctgc ctatacagtt gaactcggta cagaagtaaa tgagttcgcc   2880
tgtgttgtgg cagatgctgt cataaaaact ttgcaaccag tatctgaatt acttacacca   2940
ctgggcattg atttagatga gtggagtatg gctacatact acttatttga tgagtctggt   3000
gagtttaaat tggcttcaca tatgtattgt tctttctacc ctccagatga ggatgaagaa   3060
gaaggtgatt gtgaagaaga agagtttgag ccatcaactc aatatgagta tggtactgaa   3120
gatgattacc aaggtaaacc tttggaattt ggtgccactt ctgctgctct tcaacctgaa   3180
gaagagcaag aagaagattg gttagatgat gatagtcaac aaactgttgg tcaacaagac   3240
ggcagtgagg acaatcagac aactactatt caaacaattg ttgaggttca acctcaatta   3300
gagatggaac ttacaccagt tgttcagact attgaagtga atagttttag tggttattta   3360
aaacttactg acaatgtata cattaaaaat gcagacattg tggaagaagc taaaaaggta   3420
aaaccaacag tggttgttaa tgcagccaat gtttacctta aacatggagg aggtgttgca   3480
ggagccttaa ataaggctac taacaatgcc atgcaagttg aatctgatga ttacatagct   3540
actaatggac cacttaaagt gggtggtagt tgtgttttaa gcggacacaa tcttgctaaa   3600
cactgtcttc atgttgtcgg cccaaatgtt aacaaaggtg aagacattca acttcttaag   3660
agtgcttatg aaaattttaa tcagcacgaa gttctacttg caccattatt atcagctggt   3720
atttttggtg ctgaccctat acattcttta agagtttgtg tagatactgt tcgcacaaat   3780
gtctacttag ctgtctttga taaaaatctc tatgacaaac ttgtttcaag ctttttggaa   3840
atgaagagtg aaaagcaagt tgaacaaaag atcgctgaga ttcctaaaga ggaagttaag   3900
ccatttataa ctgaaagtaa accttcagtt gaacagagaa aacaagatga taagaaaatc   3960
aaagcttgtg ttgaagaagt tacaacaact ctggaagaaa ctaagttcct cacagaaaac   4020
ttgttacttt atattgacat taatggcaat cttcatccag attctgccac tcttgttagt   4080
gacattgaca tcactttctt aaagaaagat gctccatata tagtgggtga tgttgttcaa   4140
gagggtgttt taactgctgt ggttatacct actaaaaagg ctggtggcac tactgaaatg   4200
ctagcgaaag ctttgagaaa agtgccaaca gacaattata taaccactta cccgggtcag   4260
ggtttaaatg gttacactgt agaggaggca aagacagtgc ttaaaaagtg taaaagtgcc   4320
ttttacattc taccatctat tatctctaat gagaagcaag aaattcttgg aactgtttct   4380
tggaatttgc gagaaatgct tgcacatgca gaagaaacac gcaaattaat gcctgtctgt   4440
gtggaaacta aagccatagt ttcaactata cagcgtaaat ataagggtat taaaatacaa   4500
gagggtgtgg ttgattatgg tgctagattt tacttttaca ccagtaaaac aactgtagcg   4560
tcacttatca acacacttaa cgatctaaat gaaactcttg ttacaatgcc acttggctat   4620
gtaacacatg gcttaaattt ggaagaagct gctcggtata tgagatctct caaagtgcca   4680
```

-continued

```
gctacagttt ctgtttcttc acctgatgct gttacagcgt ataatggtta tcttacttct   4740
tcttctaaaa cacctgaaga acattttatt gaaaccatct cacttgctgg ttcctataaa   4800
gattggtcct attctggaca atctacacaa ctaggtatag aatttcttaa gagaggtgat   4860
aaaagtgtat attacactag taatcctacc acattccacc tagatggtga agttatcacc   4920
tttgacaatc ttaagacact tctttctttg agagaagtga ggactattaa ggtgtttaca   4980
acagtagaca acattaacct ccacacgcaa gttgtggaca tgtcaatgac atatggacaa   5040
cagtttggtc caacttattt ggatggagct gatgttacta aaataaaacc tcataattca   5100
catgaaggta aaacatttta tgttttacct aatgatgaca ctctacgtgt tgaggctttt   5160
gagtactacc acacaactga tcctagtttt ctgggtaggt acatgtcagc attaaatcac   5220
actaaaaagt ggaaataccc acaagttaat ggtttaactt ctattaaatg ggcagataac   5280
aactgttatc ttgccactgc attgttaaca ctccaacaaa tagagttgaa gtttaatcca   5340
cctgctctac aagatgctta ttacagagca agggctggtg aagctgctaa cttttgtgca   5400
cttatcttag cctactgtaa taagacagta ggtgagttag gtgatgttag agaaacaatg   5460
agttacttgt ttcaacatgc caatttagat tcttgcaaaa gagtcttgaa cgtggtgtgt   5520
aaaacttgtg gacaacagca gacaaccctt aagggtgtag aagctgttat gtacatgggc   5580
acactttctt atgaacaatt taagaaaggt gttcagatac cttgtacgtg tggtaaacaa   5640
gctacaaaat atctagtaca acaggagtca ccttttgtta tgatgtcagc accacctgct   5700
cagtatgaac ttaagcatgg tacatttact tgtgctagtg agtacactgg taattaccag   5760
tgtggtcact ataaacatat aacttctaaa gaaactttgt attgcataga cggtgcttta   5820
cttacaaagt cctcagaata caaaggtcct attacggatg ttttctacaa agaaaacagt   5880
tacacaacaa ccataaaacc agttacttat aaattggatg gtgttgtttg tacagaaatt   5940
gaccctaagt tggacaatta ttataagaaa gacaattctt atttcacaga gcaaccaatt   6000
gatcttgtac caaaccaacc atatccaaac gcaagcttcg ataattttaa gtttgtatgt   6060
gataatatca aatttgctga tgatttaaac cagttaactg gttataagaa acctgcttca   6120
agagagctta aagttacatt tttccctgac ttaaatggtg atgtggtggc tattgattat   6180
aaacactaca caccctcttt taagaaagga gctaaattgt tacataaacc tattgtttgg   6240
catgttaaca atgcaactaa taaagccacg tataaaccaa atacctggtg tatacgttgt   6300
ctttggagca caaaaccagt tgaaacatca aattcgtttg atgtactgaa gtcagaggac   6360
gcgcagggaa tggataatct tgcctgcgaa gatctaaaac cagtctctga agaagtagtg   6420
gaaaatccta ccatacagaa agacgttctt gagtgtaatg tgaaaactac cgaagttgta   6480
ggagacatta tacttaaacc agcaaataat agtttaaaaa ttacagaaga ggttggccac   6540
acagatctaa tggctgctta tgtagacaat tctagtctta ctattaagaa acctaatgaa   6600
ttatctagag tattaggttt gaaaaccctt gctactcatg gtttagctgc tgttaatagt   6660
gtcccttggg atactatagc taattatgct aagccttttc ttaacaaagt tgttagtaca   6720
actactaaca tagttacacg gtgtttaaac cgtgtttgta ctaattatat gccttatttc   6780
tttactttat tgctacaatt gtgtactttt actagaagta caaattctag aattaaagca   6840
tctatgccga ctactatagc aaagaatact gttaagagtg tcggtaaatt ttgtctagag   6900
gcttcattta attatttgaa gtcacctaat ttttctaaac tgataaatat tataatttgg   6960
tttttactat taagtgtttg cctaggttct ttaatctact caaccgctgc tttaggtgtt   7020
ttaatgtcta atttaggcat gccttcttac tgtactggtt acagagaagg ctatttgaac   7080
```

-continued

```
tctactaatg tcactattgc aacctactgt actggttcta taccttgtag tgtttgtctt   7140

agtggtttag attctttaga cacctatcct tctttagaaa ctatacaaat taccatttca   7200

tcttttaaat gggatttaac tgcttttggc ttagttgcag agtggttttt ggcatatatt   7260

cttttcacta ggtttttcta tgtacttgga ttggctgcaa tcatgcaatt gtttttcagc   7320

tattttgcag tacattttat tagtaattct tggcttatgt ggttaataat taatcttgta   7380

caaatggccc cgatttcagc tatggttaga atgtacatct tctttgcatc attttattat   7440

gtatggaaaa gttatgtgca tgttgtagac ggttgtaatt catcaacttg tatgatgtgt   7500

tacaaacgta atagagcaac aagagtcgaa tgtacaacta ttgttaatgg tgttagaagg   7560

tccttttatg tctatgctaa tggaggtaaa ggcttttgca aactacacaa ttggaattgt   7620

gttaattgtg atacattctg tgctggtagt acatttatta gtgatgaagt tgcgagagac   7680

ttgtcactac agtttaaaag accaataaat cctactgacc agtcttctta catcgttgat   7740

agtgttacag tgaagaatgg ttccatccat ctttactttg ataaagctgg tcaaaagact   7800

tatgaaagac attctctctc tcattttgtt aacttagaca acctgagagc taataacact   7860

aaaggttcat tgcctattaa tgttatagtt tttgatggta aatcaaaatg tgaagaatca   7920

tctgcaaaat cagcgtctgt ttactacagt cagcttatgt gtcaacctat actgttacta   7980

gatcaggcat tagtgtctga tgttggtgat agtgcggaag ttgcagttaa aatgtttgat   8040

gcttacgtta atacgttttc atcaactttt aacgtaccaa tggaaaaact caaaacacta   8100

gttgcaactg cagaagctga acttgcaaag aatgtgtcct tagacaatgt cttatctact   8160

tttatttcag cagctcggca agggtttgtt gattcagatg tagaaactaa agatgttgtt   8220

gaatgtctta aattgtcaca tcaatctgac atagaagtta ctggcgatag ttgtaataac   8280

tatatgctca cctataacaa agttgaaaac atgacacccc gtgaccttgg tgcttgtatt   8340

gactgtagtg cgcgtcatat taatgcgcag gtagcaaaaa gtcacaacat tgctttgata   8400

tggaacgtta aagatttcat gtcattgtct gaacaactac gaaaacaaat acgtagtgct   8460

gctaaaaaga ataacttacc ttttaagttg acatgtgcaa ctactagaca agttgttaat   8520

gttgtaacaa caaagatagc acttaagggt ggtaaaattg ttaataattg gttgaagcag   8580

ttaattaaag ttacacttgt gttccttttt gttgctgcta ttttctattt aataacacct   8640

gttcatgtca tgtctaaaca tactgacttt tcaagtgaaa tcataggata caaggctatt   8700

gatggtggtg tcactcgtga catagcatct acagatactt gttttgctaa caaacatgct   8760

gattttgaca catggtttag ccagcgtggt ggtagttata ctaatgacaa agcttgccca   8820

ttgattgctg cagtcataac aagagaagtg ggttttgtcg tgcctggttt gcctggcacg   8880

atattacgca caactaatgg tgactttttg catttcttac ctagagtttt tagtgcagtt   8940

ggtaacatct gttacacacc atcaaaactt atagagtaca ctgactttgc aacatcagct   9000

tgtgttttgg ctgctgaatg tacaattttt aaagatgctt ctggtaagcc agtaccatat   9060

tgttatgata ccaatgtact agaaggttct gttgcttatg aaagtttacg ccctgacaca   9120

cgttatgtgc tcatggatgg ctctattatt caatttccta acacctacct tgaaggttct   9180

gttagagtgg taacaacttt tgattctgag tactgtaggc acggcacttg tgaaagatca   9240

gaagctggtg tttgtgtatc tactagtggt agatgggtac ttaacaatga ttattacaga   9300

tctttaccag gagttttctg tggtgtagat gctgtaaatt tacttactaa tatgtttaca   9360

ccactaattc aacctattgg tgctttggac atatcagcat ctatagtagc tggtggtatt   9420
```

```
gtagctatcg tagtaacatg ccttgcctac tattttatga ggtttagaag agcttttggt   9480
gaatacagtc atgtagttgc ctttaatact ttactattcc ttatgtcatt cactgtactc   9540
tgtttaacac cagtttactc attcttacct ggtgtttatt ctgttattta cttgtacttg   9600
acattttatc ttactaatga tgtttctttt ttagcacata ttcagtggat ggttatgttc   9660
acacctttag tacctttctg gataacaatt gcttatatca tttgtatttc cacaaagcat   9720
ttctattggt tctttagtaa ttacctaaag agacgtgtag tctttaatgg tgtttccttt   9780
agtacttttg aagaagctgc gctgtgcacc tttttgttaa ataaagaaat gtatctaaag   9840
ttgcgtagtg atgtgctatt acctcttacg caatataata gatacttagc tctttataat   9900
aagtacaagt attttagtgg agcaatggat acaactagct acagagaagc tgcttgttgt   9960
catctcgcaa aggctctcaa tgacttcagt aactcaggtt ctgatgttct ttaccaacca  10020
ccacaaacct ctatcacctc agctgttttg cagagtggtt ttagaaaaat ggcattccca  10080
tctggtaaag ttgagggttg tatggtacaa gtaacttgtg gtacaactac acttaacggt  10140
ctttggcttg atgacgtagt ttactgtcca agacatgtga tctgcacctc tgaagacatg  10200
cttaacccta attatgaaga tttactcatt cgtaagtcta atcataattt cttggtacag  10260
gctggtaatg ttcaactcag ggttattgga cattctatgc aaaattgtgt acttaagctt  10320
aaggttgata cagccaatcc taagacacct aagtataagt ttgttcgcat tcaaccagga  10380
cagacttttt cagtgttagc ttgttacaat ggttcaccat ctggtgttta ccaatgtgct  10440
atgaggccca atttcactat taagggttca ttccttaatg gttcatgtgg tagtgttggt  10500
tttaacatag attatgactg tgtctctttt tgttacatgc accatatgga attaccaact  10560
ggagttcatg ctggcacaga cttagaaggt aacttttatg gaccttttgt tgacaggcaa  10620
acagcacaag cagctggtac ggacacaact attacagtta atgttttagc ttggttgtac  10680
gctgctgtta taaatggaga caggtggttt ctcaatcgat ttaccacaac tcttaatgac  10740
tttaaccttg tggctatgaa gtacaattat gaacctctaa cacaagacca tgttgacata  10800
ctaggacctc tttctgctca aactggaatt gccgttttag atatgtgtgc ttcattaaaa  10860
gaattactgc aaaatggtat gaatggacgt accatattgg gtagtgcttt attagaagat  10920
gaatttacac cttttgatgt tgttagacaa tgctcaggtg ttactttcca aagtgcagtg  10980
aaaagaacaa tcaagggtac acaccactgg ttgttactca caattttgac ttcactttta  11040
gttttagtcc agagtactca atggtctttg ttcttttttt tgtatgaaaa tgccttttta  11100
ccttttgcta tgggtattat tgctatgtct gcttttgcaa tgatgtttgt caaacataag  11160
catgcatttc tctgtttgtt tttgttacct tctcttgcca ctgtagctta ttttaatatg  11220
gtctatatgc ctgctagttg ggtgatgcgt attatgacat ggttggatat ggttgatact  11280
agtttgtctg gttttaagct aaaagactgt gttatgtatg catcagctgt agtgttacta  11340
atccttatga cagcaagaac tgtgtatgat gatggtgcta ggagagtgtg gacacttatg  11400
aatgtcttga cactcgttta taaagtttat tatggtaatg ctttagatca agccatttcc  11460
atgtgggctc ttataatctc tgttacttct aactactcag gtgtagttac aactgtcatg  11520
tttttggcca gaggtattgt ttttatgtgt gttgagtatt gccctatttt cttcataact  11580
ggtaatacac ttcagtgtat aatgctagtt tattgtttct taggctattt ttgtacttgt  11640
tactttggcc tcttttgttt actcaaccgc tactttagac tgactcttgg tgtttatgat  11700
tacttagttt ctacacagga gtttagatat atgaattcac agggactact cccacccaag  11760
aatagcatag atgccttcaa actcaacatt aaattgttgg gtgttggtgg caaaccttgt  11820
```

-continued

```
atcaaagtag ccactgtaca gtctaaaatg tcagatgtaa agtgcacatc agtagtctta  11880
ctctcagttt tgcaacaact cagagtagaa tcatcatcta aattgtgggc tcaatgtgtc  11940
cagttacaca atgacattct cttagctaaa gatactactg aagcctttga aaaaatggtt  12000
tcactacttt ctgttttgct ttccatgcag ggtgctgtag acataaacaa gctttgtgaa  12060
gaaatgctgg acaacagggc aaccttacaa gctatagcct cagagtttag ttcccttcca  12120
tcatatgcag cttttgctac tgctcaagaa gcttatgagc aggctgttgc taatggtgat  12180
tctgaagttg ttcttaaaaa gttgaagaag tctttgaatg tggctaaatc tgaatttgac  12240
cgtgatgcag ccatgcaacg taagttggaa aagatggctg atcaagctat gacccaaatg  12300
tataaacagg ctagatctga ggacaagagg gcaaaagtta ctagtgctat gcagacaatg  12360
cttttcacta tgcttagaaa gttggataat gatgcactca acaacattat caacaatgca  12420
agagatggtt gtgttccctt gaacataata cctcttacaa cagcagccaa actaatggtt  12480
gtcataccag actataacac atataaaaat acgtgtgatg gtacaacatt tacttatgca  12540
tcagcattgt gggaaatcca acaggttgta gatgcagata gtaaaattgt tcaacttagt  12600
gaaattagta tggacaattc acctaattta gcatggcctc ttattgtaac agctttaagg  12660
gccaattctg ctgtcaaatt acagaataat gagcttagtc ctgttgcact acgacagatg  12720
tcttgtgctg ccggtactac acaaactgct tgcactgatg acaatgcgtt agcttactac  12780
aacacaacaa agggaggtag gtttgtactt gcactgttat ccgatttaca ggatttgaaa  12840
tgggctagat tccctaagag tgatggaact ggtactatct atacagaact ggaaccacct  12900
tgtaggtttg ttacagacac acctaaaggt cctaaagtga agtatttata ctttattaaa  12960
ggattaaaca acctaaatag aggtatggta cttggtagtt tagctgccac agtacgtcta  13020
caagctggta atgcaacaga agtgcctgcc aattcaactg tattatcttt ctgtgctttt  13080
gctgtagatg ctgctaaagc ttacaaagat tatctagcta gtgggggaca accaatcact  13140
aattgtgtta agatgttgtg tacacacact ggtactggtc aggcaataac agttacaccg  13200
gaagccaata tggatcaaga atcctttggt ggtgcatcgt gttgtctgta ctgccgttgc  13260
cacatagatc atccaaatcc taaaggattt tgtgacttaa aaggtaagta tgtacaaata  13320
cctacaactt gtgctaatga ccctgtgggt tttacactta aaaacacagt ctgtaccgtc  13380
tgcggtatgt ggaaaggtta tggctgtagt tgtgatcaac tccgcgaacc catgcttcag  13440
tcagctgatg cacaatcgtt tttaaacggg tttgcggtgt aagtgcagcc cgtcttacac  13500
cgtgcggcac aggcactagt actgatgtcg tatacagggc ttttgacatc tacaatgata  13560
aagtagctgg ttttgctaaa ttcctaaaaa ctaattgttg tcgcttccaa gaaaaggacg  13620
aagatgacaa tttaattgat tcttactttg tagttaagag acacactttc tctaactacc  13680
aacatgaaga aacaatttat aatttactta aggattgtcc agctgttgct aaacatgact  13740
tctttaagtt tagaatagac ggtgacatgg taccacatat atcacgtcaa cgtcttacta  13800
aatacacaat ggcagacctc gtctatgctt taaggcattt tgatgaaggt aattgtgaca  13860
cattaaaaga aatacttgtc acatacaatt gttgtgatga tgattatttc aataaaaagg  13920
actggtatga ttttgtagaa aacccagata tattacgcgt atacgccaac ttaggtgaac  13980
gtgtacgcca agctttgtta aaaacagtac aattctgtga tgccatgcga aatgctggta  14040
ttgttggtgt actgacatta gataatcaag atctcaatgg taactggtat gatttcggtg  14100
atttcataca aaccacgcca ggtagtggag ttcctgttgt agattcttat tattcattgt  14160
```

-continued

```
taatgcctat attaaccttg accagggctt taactgcaga gtcacatgtt gacactgact  14220
taacaaagcc ttacattaag tgggatttgt taaaatatga cttcacggaa gagaggttaa  14280
aactctttga ccgttatttt aaatattggg atcagacata ccacccaaat tgtgttaact  14340
gtttggatga cagatgcatt ctgcattgtg caaactttaa tgttttattc tctacagtgt  14400
tcccacctac aagttttgga ccactagtga gaaaaatatt tgttgatggt gttccatttg  14460
tagtttcaac tggataccac ttcagagagc taggtgttgt acataatcag gatgtaaact  14520
tacatagctc tagacttagt tttaaggaat tacttgtgta tgctgctgac cctgctatgc  14580
acgctgcttc tggtaatcta ttactagata aacgcactac gtgcttttca gtagctgcac  14640
ttactaacaa tgttgctttt caaactgtca aacccggtaa ttttaacaaa gacttctatg  14700
actttgctgt gtctaagggt ttctttaagg aaggaagttc tgttgaatta aaacacttct  14760
tctttgctca ggatggtaat gctgctatca gcgattatga ctactatcgt tataatctac  14820
caacaatgtg tgatatcaga caactactat ttgtagttga agttgttgat aagtactttg  14880
attgttacga tggtggctgt attaatgcta accaagtcat cgtcaacaac ctagacaaat  14940
cagctggttt tccatttaat aaatggggta aggctagact ttattatgat tcaatgagtt  15000
atgaggatca agatgcactt ttcgcatata caaaacgtaa tgtcatccct actataactc  15060
aaatgaatct taagtatgcc attagtgcaa agaatagagc tcgcaccgta gctggtgtct  15120
ctatctgtag tactatgacc aatagacagt ttcatcaaaa attattgaaa tcaatagccg  15180
ccactagagg agctactgta gtaattggaa caagcaaatt ctatggtggt tggcacaaca  15240
tgttaaaaac tgtttatagt gatgtagaaa accctcacct tatgggttgg gattatccta  15300
aatgtgatag agccatgcct aacatgctta gaattatggc ctcacttgtt cttgctcgca  15360
aacatacaac gtgttgtagc ttgtcacacc gtttctatag attagctaat gagtgtgctc  15420
aagtattgag tgaaatggtc atgtgtggcg gttcactata tgttaaacca ggtggaacct  15480
catcaggaga tgccacaact gcttatgcta atagtgtttt taacatttgt caagctgtca  15540
cggccaatgt taatgcactt ttatctactg atggtaacaa aattgccgat aagtatgtcc  15600
gcaatttaca acacagactt tatgagtgtc tctatagaaa tagagatgtt gacacagact  15660
ttgtgaatga gttttacgca tatttgcgta aacatttctc aatgatgata ctctctgacg  15720
atgctgttgt gtgtttcaat agcacttatg catctcaagg tctagtggct agcataaaga  15780
actttaagtc agttctttat tatcaaaaca atgtttttat gtctgaagca aaatgttgga  15840
ctgagactga ccttactaaa ggacctcatg aattttgctc tcaacataca atgctagtta  15900
aacagggtga tgattatgtg taccttcctt acccagatcc atcaagaatc ctaggggccg  15960
gctgttttgt agatgatatc gtaaaaacag atggtacact tatgattgaa cggttcgtgt  16020
ctttagctat agatgcttac ccacttacta aacatcctaa tcaggagtat gctgatgtct  16080
ttcatttgta cttacaatac ataagaaagc tacatgatga gttaacagga cacatgttag  16140
acatgtattc tgttatgctt actaatgata acacttcaag gtattgggaa cctgagtttt  16200
atgaggctat gtacacaccg catacagtct tacaggctgt tggggcttgt gttctttgca  16260
attcacagac ttcattaaga tgtggtgctt gcatacgtag accattctta tgttgtaaat  16320
gctgttacga ccatgtcata tcaacatcac ataaattagt cttgtctgtt aatccgtatg  16380
tttgcaatgc tccaggttgt gatgtcacag atgtgactca actttactta ggaggtatga  16440
gctattattg taaatcacat aaaccaccca ttagttttcc attgtgtgct aatggacaag  16500
tttttggttt atataaaaat acatgtgttg gtagcgataa tgttactgac tttaatgcaa  16560
```

```
ttgcaacatg tgactggaca aatgctggtg attacatttt agctaacacc tgtactgaaa  16620
gactcaagct ttttgcagca gaaacgctca aagctactga ggagacattt aaactgtctt  16680
atggtattgc tactgtacgt gaagtgctgt ctgacagaga attacatctt tcatgggaag  16740
ttggtaaacc tagaccacca cttaaccgaa attatgtctt tactggttat cgtgtaacta  16800
aaaacagtaa agtacaaata ggagagtaca cctttgaaaa aggtgactat ggtgatgctg  16860
ttgtttaccg aggtacaaca acttacaaat taaatgttgg tgattatttt gtgctgacat  16920
cacatacagt aatgccatta agtgcaccta cactagtgcc acaagagcac tatgttagaa  16980
ttactggctt atacccaaca ctcaatatct cagatgagtt ttctagcaat gttgcaaatt  17040
atcaaaaggt tggtatgcaa aagtattcta cactccaggg accacctggt actggtaaga  17100
gtcattttgc tattggccta gctctctact acccttctgc tcgcatagtg tatacagctt  17160
gctctcatgc cgctgttgat gcactatgtg agaaggcatt aaaatatttg cctatagata  17220
aatgtagtag aattatacct gcacgtgctc gtgtagagtg ttttgataaa ttcaaagtga  17280
attcaacatt agaacagtat gtcttttgta ctgtaaatgc attgcctgag acgacagcag  17340
atatagttgt ctttgatgaa atttcaatgg ccacaaatta tgatttgagt gttgtcaatg  17400
ccagattacg tgctaagcac tatgtgtaca ttggcgaccc tgctcaatta cctgcaccac  17460
gcacattgct aactaagggc acactagaac cagaatattt caattcagtg tgtagactta  17520
tgaaaactat aggtccagac atgttcctcg gaacttgtcg gcgttgtcct gctgaaattg  17580
ttgacactgt gagtgctttg gtttatgata ataagcttaa agcacataaa gacaaatcag  17640
ctcaatgctt taaaatgttt tataagggtg ttatcacgca tgatgtttca tctgcaatta  17700
acaggccaca aataggcgtg gtaagagaat tccttacacg taaccctgct tggagaaaag  17760
ctgtctttat ttcaccttat aattcacaga atgctgtagc ctcaaagatt ttgggactac  17820
caactcaaac tgttgattca tcacagggct cagaatatga ctatgtcata ttcactcaaa  17880
ccactgaaac agctcactct tgtaatgtaa acagatttaa tgttgctatt accagagcaa  17940
aagtaggcat actttgcata atgtctgata gagaccttta tgacaagttg caatttacaa  18000
gtcttgaaat tccacgtagg aatgtggcaa ctttacaagc tgaaaatgta acaggactct  18060
ttaaagattg tagtaaggta atcactgggt tacatcctac acaggcacct acacacctca  18120
gtgttgacac taaattcaaa actgaaggtt tatgtgttga catacctggc atacctaagg  18180
acatgaccta tagaagactc atctctatga tgggttttaa aatgaattat caagttaatg  18240
gttaccctaa catgtttatc acccgcgaag aagctataag acatgtacgt gcatggattg  18300
gcttcgatgt cgaggggtgt catgctacta gagaagctgt tggtaccaat ttacctttac  18360
agctaggttt ttctacaggt gttaacctag ttgctgtacc tacaggttat gttgatacac  18420
ctaataatac agatttttcc agagttagtg ctaaaccacc gcctggagat caatttaaac  18480
acctcatacc acttatgtac aaaggacttc cttggaatgt agtgcgtata aagattgtac  18540
aaatgttaag tgacacactt aaaaatctct ctgacagagt cgtatttgtc ttatgggcac  18600
atggctttga gttgacatct atgaagtatt ttgtgaaaat aggacctgag cgcacctgtt  18660
gtctatgtga tagacgtgcc acatgctttt ccactgcttc agacacttat gcctgttggc  18720
atcattctat tggatttgat tacgtctata atccgtttat gattgatgtt caacaatggg  18780
gttttacagg taacctacaa agcaaccatg atctgtattg tcaagtccat ggtaatgcac  18840
atgtagctag ttgtgatgca atcatgacta ggtgtctagc tgtccacgag tgctttgtta  18900
```

-continued

```
agcgtgttga ctggactatt gaatatccta taattggtga tgaactgaag attaatgcgg  18960
cttgtagaaa ggttcaacac atggttgtta aagctgcatt attagcagac aaattcccag  19020
ttcttcacga cattggtaac cctaaagcta ttaagtgtgt acctcaagct gatgtagaat  19080
ggaagttcta tgatgcacag ccttgtagtg acaaagctta taaaatagaa gaattattct  19140
attcttatgc cacacattct gacaaattca cagatggtgt atgcctattt tggaattgca  19200
atgtcgatag atatcctgct aattccattg tttgtagatt tgacactaga gtgctatcta  19260
accttaactt gcctggttgt gatggtggca gtttgtatgt aaataaacat gcattccaca  19320
caccagcttt tgataaaagt gcttttgtta atttaaaaca attaccattt ttctattact  19380
ctgacagtcc atgtgagtct catggaaaac aagtagtgtc agatatagat tatgtaccac  19440
taaagtctgc tacgtgtata acacgttgca atttaggtgg tgctgtctgt agacatcatg  19500
ctaatgagta cagattgtat ctcgatgctt ataacatgat gatctcagct ggctttagct  19560
tgtgggttta caaacaattt gatacttata acctctggaa cacttttaca agacttcaga  19620
gtttagaaaa tgtggctttt aatgttgtaa ataagggaca ctttgatgga caacagggtg  19680
aagtaccagt ttctatcatt aataacactg tttacacaaa agttgatggt gttgatgtag  19740
aattgtttga aaataaaaca acattacctg ttaatgtagc atttgagctt tgggctaagc  19800
gcaacattaa accagtacca gaggtgaaaa tactcaataa tttgggtgtg gacattgctg  19860
ctaatactgt gatctgggac tacaaaagag atgctccagc acatatatct actattggtg  19920
tttgttctat gactgacata gccaagaaac caactgaaac gatttgtgca ccactcactg  19980
tctttttga tggtagagtt gatggtcaag tagacttatt tagaaatgcc cgtaatggtg  20040
ttcttattac agaaggtagt gttaaaggtt tacaaccatc tgtaggtccc aaacaagcta  20100
gtcttaatgg agtcacatta attggagaag ccgtaaaaac acagttcaat tattataaga  20160
aagttgatgg tgttgtccaa caattacctg aaacttactt tactcagagt agaaatttac  20220
aagaatttaa acccaggagt caaatggaaa ttgatttctt agaattagct atggatgaat  20280
tcattgaacg gtataaatta gaaggctatg ccttcgaaca tatcgtttat ggagatttta  20340
gtcatagtca gttaggtggt ttacatctac tgattggact agctaaacgt tttaaggaat  20400
caccttttga attagaagat tttattccta tggacagtac agttaaaaac tatttcataa  20460
cagatgcgca aacaggttca tctaagtgtg tgtgttctgt tattgattta ttacttgatg  20520
attttgttga aataataaaa tcccaagatt tatctgtagt ttctaaggtt gtcaaagtga  20580
ctattgacta tacagaaatt tcatttatgc tttggtgtaa agatggccat gtagaaacat  20640
tttacccaaa attacaatct agtcaagcgt ggcaaccggg tgttgctatg cctaatcttt  20700
acaaaatgca aagaatgcta ttagaaaagt gtgaccttca aaattatggt gatagtgcaa  20760
cattacctaa aggcataatg atgaatgtcg caaaatatac tcaactgtgt caatatttaa  20820
acacattaac attagctgta ccctataata tgagagttat acattttggt gctggttctg  20880
ataaaggagt tgcaccaggt acagctgttt taagacagtg gttgcctacg ggtacgctgc  20940
ttgtcgattc agatcttaat gactttgtct ctgatgcaga ttcaactttg attggtgatt  21000
gtgcaactgt acatacagct aataaatggg atctcattat tagtgatatg tacgacccta  21060
agactaaaaa tgttacaaaa gaaaatgact ctaaagaggg tttttcact tacatttgtg  21120
ggtttataca acaaaagcta gctcttggag gttccgtggc tataaagata acagaacatt  21180
cttggaatgc tgatctttat aagctcatgg gacacttcgc atggtggaca gcctttgtta  21240
ctaatgtgaa tgcgtcatca tctgaagcat tttaattgg atgtaattat cttggcaaac  21300
```

```
cacgcgaaca aatagatggt tatgtcatgc atgcaaatta catattttgg aggaatacaa  21360
atccaattca gttgtcttcc tattctttat ttgacatgag taaatttccc cttaaattaa  21420
ggggtactgc tgttatgtct ttaaaagaag gtcaaatcaa tgatatgatt ttatctcttc  21480
ttagtaaagg tagacttata attagagaaa acaacagagt tgttatttct agtgatgttc  21540
ttgttaacaa ctaaacgaac aatgtttgtt tttcttgttt tattgccact agtctctagt  21600
cagtgtgtta atcttacaac cagaactcaa ttaccccctg catacactaa ttctttcaca  21660
cgtggtgttt attaccctga caaagttttc agatcctcag ttttacattc aactcaggac  21720
ttgttcttac ctttcttttc caatgttact tggttccatg ctatacatgt ctctgggacc  21780
aatggtacta agaggtttga taaccctgtc ctaccattta atgatggtgt ttattttgct  21840
tccactgaga agtctaacat aataagaggc tggatttttg gtactacttt agattcgaag  21900
acccagtccc tacttattgt taataacgct actaatgttg ttattaaagt ctgtgaattt  21960
caattttgta atgatccatt tttgggtgtt tattaccaca aaaacaacaa aagttggatg  22020
gaaagtgagt tcagagttta ttctagtgcg aataattgca cttttgaata tgtctctcag  22080
ccttttctta tggaccttga aggaaaacag ggtaatttca aaaatcttag ggaatttgtg  22140
tttaagaata ttgatggtta ttttaaaata tattctaagc acacgcctat taatttagtg  22200
cgtgatctcc ctcagggttt ttcggcttta gaaccattgg tagatttgcc aataggtatt  22260
aacatcacta ggtttcaaac tttacttgct ttacatagaa gttatttgac tcctggtgat  22320
tcttcttcag gttggacagc tggtgctgca gcttattatg tgggttatct tcaacctagg  22380
acttttctat taaaatataa tgaaaatgga accattacag atgctgtaga ctgtgcactt  22440
gaccctctct cagaaacaaa gtgtacgttg aaatccttca ctgtagaaaa aggaatctat  22500
caaacttcta actttagagt ccaaccaaca gaatctattg ttagatttcc taatattaca  22560
aacttgtgcc cttttggtga agtttttaac gccaccagat ttgcatctgt ttatgcttgg  22620
aacaggaaga gaatcagcaa ctgtgttgct gattattctg tcctatataa ttccgcatca  22680
ttttccactt ttaagtgtta tggagtgtct cctactaaat taaatgatct ctgctttact  22740
aatgtctatg cagattcatt tgtaattaga ggtgatgaag tcagacaaat cgctccaggg  22800
caaactggaa agattgctga ttataattat aaattaccag atgattttac aggctgcgtt  22860
atagcttgga attctaacaa tcttgattct aaggttggtg gtaattataa ttacctgtat  22920
agattgttta ggaagtctaa tctcaaacct tttgagagag atatttcaac tgaaatctat  22980
caggccggta gcacaccttg taatggtgtt gaaggtttta attgttactt tcctttacaa  23040
tcatatggtt tccaacccac taatggtgtt ggttaccaac catacagagt agtagtactt  23100
tcttttgaac ttctacatgc accagcaact gtttgtggac ctaaaaagtc tactaatttg  23160
gttaaaaaca aatgtgtcaa tttcaacttc aatggtttaa caggcacagg tgttcttact  23220
gagtctaaca aaaagtttct gcctttccaa caatttggca gagacattgc tgacactact  23280
gatgctgtcc gtgatccaca gacacttgag attcttgaca ttacaccatg ttcttttggt  23340
ggtgtcagtg ttataacacc aggaacaaat acttctaacc aggttgctgt tctttatcag  23400
gatgttaact gcacagaagt ccctgttgct attcatgcag atcaacttac tcctacttgg  23460
cgtgtttatt ctacaggttc taatgttttt caaacacgtg caggctgttt aataggggct  23520
gaacatgtca acaactcata tgagtgtgac atacccattg gtgcaggtat atgcgctagt  23580
tatcagactc agactaattc tcctcggcgg gcacgtagtg tagctagtca atccatcatt  23640
```

```
gcctacacta tgtcacttgg tgcagaaaat tcagttgctt actctaataa ctctattgcc  23700
atacccacaa attttactat tagtgttacc acagaaattc taccagtgtc tatgaccaag  23760
acatcagtag attgtacaat gtacatttgt ggtgattcaa ctgaatgcag caatcttttg  23820
ttgcaatatg gcagtttttg tacacaatta aaccgtgctt taactggaat agctgttgaa  23880
caagacaaaa acacccaaga agtttttgca caagtcaaac aaatttacaa aacaccacca  23940
attaaagatt ttggtggttt taatttttca caaatattac cagatccatc aaaaccaagc  24000
aagaggtcat ttattgaaga tctacttttc aacaaagtga cacttgcaga tgctggcttc  24060
atcaaacaat atggtgattg ccttggtgat attgctgcta gagacctcat ttgtgcacaa  24120
aagtttaacg gccttactgt tttgccacct ttgctcacag atgaaatgat tgctcaatac  24180
acttctgcac tgttagcggg tacaatcact tctggttgga cctttggtgc aggtgctgca  24240
ttacaaatac catttgctat gcaaatggct tataggttta atggtattgg agttacacag  24300
aatgttctct atgagaacca aaaattgatt gccaaccaat ttaatagtgc tattggcaaa  24360
attcaagact cactttcttc cacagcaagt gcacttggaa aacttcaaga tgtggtcaac  24420
caaaatgcac aagctttaaa cacgcttgtt aaacaactta gctccaattt tggtgcaatt  24480
tcaagtgttt taaatgatat cctttcacgt cttgacaaag ttgaggctga agtgcaaatt  24540
gataggttga tcacaggcag acttcaaagt ttgcagacat atgtgactca acaattaatt  24600
agagctgcag aaatcagagc ttctgctaat cttgctgcta ctaaaatgtc agagtgtgta  24660
cttggacaat caaaaagagt tgatttttgt ggaaagggct atcatcttat gtccttccct  24720
cagtcagcac ctcatggtgt agtcttcttg catgtgactt atgtccctgc acaagaaaag  24780
aacttcacaa ctgctcctgc catttgtcat gatggaaaag cacactttcc tcgtgaaggt  24840
gtctttgttt caaatggcac acactggttt gtaacacaaa ggaattttta tgaaccacaa  24900
atcattacta cagacaacac atttgtgtct ggtaactgtg atgttgtaat aggaattgtc  24960
aacaacacag tttatgatcc tttgcaacct gaattagact cattcaagga ggagttagat  25020
aaatatttta agaatcatac atcaccagat gttgatttag gtgacatctc tggcattaat  25080
gcttcagttg taaacattca aaaagaaatt gaccgcctca atgaggttgc caagaattta  25140
aatgaatctc tcatcgatct ccaagaactt ggaaagtatg agcagtatat aaaatggcca  25200
tggtacattt ggctaggttt tatagctggc ttgattgcca tagtaatggt gacaattatg  25260
ctttgctgta tgaccagttg ctgtagttgt ctcaagggct gttgttcttg tggatcctgc  25320
tgcaaatttg atgaagacga ctctgagcca gtgctcaaag gagtcaaatt acattacaca  25380
taaacgaact tatggatttg tttatgagaa tcttcacaat tggaactgta actttgaagc  25440
aaggtgaaat caaggatgct actccttcag attttgttcg cgctactgca acgataccga  25500
tacaagcctc actccctttc ggatggctta ttgttggcgt tgcacttctt gctgtttttc  25560
agagcgcttc caaaatcata accctcaaaa agagatggca actagcactc tccaagggtg  25620
ttcactttgt ttgcaacttg ctgttgttgt ttgtaacagt ttactcacac cttttgctcg  25680
ttgctgctgg ccttgaagcc ccttttctct atctttatgc tttagtctac ttcttgcaga  25740
gtataaactt tgtaagaata ataatgaggc tttggctttg ctggaaatgc cgttccaaaa  25800
acccattact ttatgatgcc aactattttc tttgctggca tactaattgt tacgactatt  25860
gtataccta caatagtgta acttcttcaa ttgtcattac ttcaggtgat ggcacaacaa  25920
gtcctatttc tgaacatgac taccagattg gtggttatac tgaaaaatgg gaatctggag  25980
taaaagactg tgttgtatta cacagttact tcacttcaga ctattaccag ctgtactcaa  26040
```

```
ctcaattgag tacagacact ggtgttgaac atgttacctt cttcatctac aataaaattg  26100
ttgatgagcc tgaagaacat gtccaaattc acacaatcga cggttcatcc ggagttgtta  26160
atccagtaat ggaaccaatt tatgatgaac cgacgacgac tactagcgtg cctttgtaag  26220
cacaagctga tgagtacgaa cttatgtact cattcgtttc ggaagagaca ggtacgttaa  26280
tagttaatag cgtacttctt tttcttgctt tcgtggtatt cttgctagtt acactagcca  26340
tccttactgc gcttcgattg tgtgcgtact gctgcaatat tgttaacgtg agtcttgtaa  26400
aaccttcttt ttacgtttac tctcgtgtta aaaatctgaa ttcttctaga gttcctgatc  26460
ttctggtcta aacgaactaa atattatatt agtttttctg tttggaactt taattttagc  26520
catggcagat tccaacggta ctattaccgt tgaagagctt aaaaagctcc ttgaacaatg  26580
gaacctagta ataggtttcc tattccttac atggatttgt cttctacaat ttgcctatgc  26640
caacaggaat aggtttttgt atataattaa gttaatttc ctctggctgt tatggccagt  26700
aactttagct tgttttgtgc ttgctgctgt ttacagaata aattggatca ccggtggaat  26760
tgctatcgca atggcttgtc ttgtaggctt gatgtggctc agctacttca ttgcttcttt  26820
cagactgttt gcgcgtacgc gttccatgtg gtcattcaat ccagaaacta acattcttct  26880
caacgtgcca ctccatggca ctattctgac cagaccgctt ctagaaagtg aactcgtaat  26940
cggagctgtg atccttcgtg gacatcttcg tattgctgga caccatctag gacgctgtga  27000
catcaaggac ctgcctaaag aaatcactgt tgctacatca cgaacgcttt cttattacaa  27060
attgggagct tcgcagcgtg tagcaggtga ctcaggtttt gctgcataca gtcgctacag  27120
gattggcaac tataaattaa acacagacca ttccagtagc agtgacaata ttgctttgct  27180
tgtacagtaa gtgacaacag atgtttcatc tcgttgactt tcaggttact atagcagaga  27240
tattactaat tattatgagg acttttaaag tttccatttg gaatcttgat tacatcataa  27300
acctcataat taaaaattta tctaagtcac taactgagaa taaatattct caattagatg  27360
aagagcaacc aatggagatt gattaaacga acatgaaaat tattcttttc ttggcactga  27420
taacactcgc tacttgtgag ctttatcact accaagagtg tgttagaggt acaacagtac  27480
ttttaaaaga accttgctct tctggaacat acgagggcaa ttcaccattt catcctctag  27540
ctgataacaa atttgcactg acttgcttta gcactcaatt tgcttttgct tgtcctgacg  27600
gcgtaaaaca cgtctatcag ttacgtgcca gatcagtttc acctaaactg ttcatcagac  27660
aagaggaagt tcaagaactt tactctccaa tttttcttat tgttgcggca atagtgttta  27720
taacactttg cttcacactc aaaagaaaga cagaatgatt gaactttcat taattgactt  27780
ctatttgtgc tttttagcct ttctgctatt ccttgtttta attatgctta ttatcttttg  27840
gttctcactt gaactgcaag atcataatga aacttgtcac gcctaaacga acatgaaatt  27900
tcttgttttc ttaggaatca tcacaactgt agctgcattt caccaagaat gtagtttaca  27960
gtcatgtact caacatcaac catatgtagt tgatgacccg tgtcctattc acttctattc  28020
taaatggtat attagagtag gagctagaaa atcagcacct ttaattgaat tgtgcgtgga  28080
tgaggctggt tctaaatcac ccattcagta catcgatatc ggtaattata cagtttcctg  28140
tttacctttt acaattaatt gccaggaacc taaattgggt agtcttgtag tgcgttgttc  28200
gttctatgaa gactttttag agtatcatga cgttcgtgtt gttttagatt tcatctaaac  28260
gaacaaacta aaatgtctga taatggaccc caaaatcagc gaaatgcacc ccgcattacg  28320
tttggtggac cctcagattc aactggcagt aaccagaatg gagaacgcag tggggcgcga  28380
```

```
tcaaaacaac gtcggcccca aggtttaccc aataatactg cgtcttggtt caccgctctc  28440

actcaacatg gcaaggaaga ccttaaattc cctcgaggac aaggcgttcc aattaacacc  28500

aatagcagtc cagatgacca aattggctac taccgaagag ctaccagacg aattcgtggt  28560

ggtgacggta aaatgaaaga tctcagtcca agatggtatt tctactacct aggaactggg  28620

ccagaagctg gacttcccta tggtgctaac aaagacggca tcatatgggt tgcaactgag  28680

ggagccttga atacaccaaa agatcacatt ggcacccgca atcctgctaa caatgctgca  28740

atcgtgctac aacttcctca aggaacaaca ttgccaaaag gcttctacgc agaagggagc  28800

agaggcggca gtcaagcctc ttctcgttcc tcatcacgta gtcgcaacag ttcaagaaat  28860

tcaactccag gcagcagtag gggaacttct cctgctagaa tggctggcaa tggcggtgat  28920

gctgctcttg ctttgctgct gcttgacaga ttgaaccagc ttgagagcaa aatgtctggt  28980

aaaggccaac aacaacaagg ccaaactgtc actaagaaat ctgctgctga ggcttctaag  29040

aagcctcggc aaaaacgtac tgccactaaa gcatacaatg taacacaagc tttcggcaga  29100

cgtggtccag aacaaaccca aggaaatttt ggggaccagg aactaatcag acaaggaact  29160

gattacaaac attggccgca aattgcacaa tttgccccca gcgcttcagc gttcttcgga  29220

atgtcgcgca ttggcatgga agtcacacct tcgggaacgt ggttgaccta cacaggtgcc  29280

atcaaattgg atgacaaaga tccaaatttc aaagatcaag tcattttgct gaataagcat  29340

attgacgcat acaaaacatt cccaccaaca gagcctaaaa aggacaaaaa gaagaaggct  29400

gatgaaactc aagccttacc gcagagacag aagaaacagc aaactgtgac tcttcttcct  29460

gctgcagatt tggatgattt ctccaaacaa ttgcaacaat ccatgagcag tgctgactca  29520

actcaggcct aaactcatgc agaccacaca aggcagatgg gctatataaa cgttttcgct  29580

tttccgttta cgatatatag tctactcttg tgcagaatga attctcgtaa ctacatagca  29640

caagtagatg tagttaactt taatctcaca tagcaatctt taatcagtgt gtaacattag  29700

ggaggacttg aaagagccac cacattttca ccgaggccac gcggagtacg atcgagtgta  29760

cagtgaacaa tgctagggag agctgcctat atggaagagc cctaatgtgt aaaattaatt  29820

ttagtagtgc tatccccatg tgattttaat agcttcttag gagaatgaca aaaaaaaaaa  29880

a                                                                  29881
```

```
<210> SEQ ID NO 13
<211> LENGTH: 110
<212> TYPE: DNA
<213> ORGANISM: Artificial Sequence
<220> FEATURE:
<223> OTHER INFORMATION: Leader synthetic construct

<400> SEQUENCE: 13

attaaaggtt tataccttcc caggtaacaa accaaccaac tttcgatctc ttgtagatct     60

gttctctaaa cgaactttaa aatctgtgtg gctgtcactc ggctgcatgc              110


<210> SEQ ID NO 14
<211> LENGTH: 4251
<212> TYPE: DNA
<213> ORGANISM: Artificial Sequence
<220> FEATURE:
<223> OTHER INFORMATION: Rnase P synthetic construct

<400> SEQUENCE: 14

atgggacttc agcatggcgg tgtttgcaga tttggacctg cgagcgggtt ctgacctgaa     60

ggctctgcgc ggacttgtgg agacagccgc tcaccttggc tattcagttg ttgctatcaa    120
```

```
tcatatcgtt gactttaagg aaaagaaaca ggaaattgaa aaaccagtag ctgtttctga    180
actcttcaca actttgccaa ttgtacaggg aaaatcaaga ccaattaaaa ttttaactag    240
attaacaatt attgtctcgg atccatctca ctgcaatgtt ttgagagcaa cttcttcaag    300
ggcccggctc tatgatgttg ttgcagtttt tccaaagaca gaaaagcttt ttcatattgc    360
ttgcacacat ttagatgtgg atttagtctg cataactgta acagagaaac taccatttta    420
cttcaaaaga cctcctatta atgtggcgat tgaccgaggc ctggcttttg aacttgtcta    480
tagccctgct atcaaagact ccacaatgag aaggtataca atttccagtg ccctcaattt    540
gatgcaaatc tgcaaaggaa agaatgtaat tatatctagt gctgcagaaa ggcctttaga    600
aataagaggg ccatatgacg tggcaaatct aggcttgctg tttgggctct ctgaaagtga    660
cgccaaggct gcggtgtcca ccaactgccg agcagcgctt ctccatggag aaactagaaa    720
aactgctttt ggaattatct ctacagtgaa gaaacctcgg ccatcagaag gagatgaaga    780
ttgtcttcca gcttccaaga aagccaagtg gtctcactct gtcacccagg ctggagtgca    840
gtggcacaat ctcggctcac tgcaaccttt gcctcttggg ctcaagccat cctcccacct    900
cagcctccca agaactagaa ttcaacaaag acaacttttg atctctcatc agagagatca    960
tactcccaag aacaggcttt gacccttctt taaaagagga ttgtcctggg ctgatgagag   1020
tcactttacc tgaagatacc tgggaagttt tgtctcctct gaggttggcc catggccagt   1080
gactgatgca ggacattaca gcctggccca ctggcctcgg tggtacaatt tatgctcctg   1140
agcaccccat gggattacgc tgtgtgtgga tttctcctga aaccacatat ttgcctcttc   1200
tgccctgttc tgttttttct cattccctta tagaggactc tcagtaagtc acttacacaa   1260
gaatcctaat ttgaaatgct gcttccagga gacctgactt agaaaattgg acaaataaag   1320
ttgatttttt taaatgtcca gtaacatgaa gatgctgaac tttcctagtc atttaggggg   1380
aaatcaccac aaatatatct ggctgatcag gttgaaagtt aaaagaaaaa aagatttata   1440
aagtgggtat tttcaagatg gtgtggaggg agatacaatt tgatgcaagt cttatacttt   1500
tgatgtcaat ttattcttca gaaataactg gttaattata aagggtggat ggataaggat   1560
attcactgca acaatgtctt aaatgtgaaa atggaaacaa cctaaatacc caataataac   1620
aggattaaat aattcattgt acattaaaag aatactgtct ataaagatgt ctagaataag   1680
ttgttcagtt gaagttgtaa agctaaatac acaataccca taatgtgcac agaaataatc   1740
agaatgtcat gaaaccagga ttattggtga tgtgttgctt cctttgttac tcatttctgt   1800
attggcataa tgagtattgg gtgttcaaga ggagggggaa ggaagtatga cagatgttat   1860
ggggaaaaag caaagtacaa caggaagaca ccttggggga actaatagaa tctaaggact   1920
caaggatggc ttcctggagg aaatacagct agaacaaagg ggaggaatga gaagtgatgt   1980
gatggcgtgg agtgggctgt agtgggaaga agagtcttcc agggagctgg cacagtatgt   2040
gaaaacagta aagcaagtgc ctggattttt taaggaactg aaaatttagt tgagttgaaa   2100
tttagagttt ggctaggaag gttatgagag ataagaataa agagttaaca gcagccagat   2160
tttaaggatt ttataagaca tttttaggag tttttatttc atcctgagag aaatgtgaag   2220
ccatcgaagg gttgaaagag gagagtgagt tgatcagcat tgcattttag aaaaatccct   2280
ctatctgcaa cttgaaaaac attctggagg taagcaagcc tggaggccag gagcctagga   2340
gggctatttg atccagatga gaagtaatgg tgacctgaac tagggcagag gcacctagga   2400
ttggaaaaca tggacagatc acagcactac ttatgtagta tacttggtaa gacctggttg   2460
```

```
tttaaaagag aaggatgagg gaaagaaggt caaaaacaac ttctaggact ctccattggc   2520
cagtgtggtg tgcccttcac tgaagagcaa acacaaaatg aaagattgtg ggcaaagagt   2580
tgagtcagtg agaaggcaag gagagaacct tataaaaaaa ttgactatgt gattaaaaac   2640
ttaaaaattt cccccaacgt gtttatcttt tccattagca gaaataacta agagttgtct   2700
taattctaat gggatttatt ccatattgtc tctcatgccc tctacctagt tattagtgca   2760
aatatttata tgtggcaaca taaaactttt taactcttta ttctcttctc tcgtgtaccc   2820
tcccagctct ttaggggagg tggatttgag gcagatacca taaagaaaag ttggtcacat   2880
ggtggtaaca cgttgaagtt atgccacatg agacatcagc actggcaaga gaaatgtctg   2940
tgttgtagat gtttcacttg gaagaaattg aaggaccctg agccttaaaa gtctgacaaa   3000
cttaagccag gacccctgtg ggaaggtag aggggccaac aaacaagatt gggagtcaga   3060
gagataacaa tgaaatcccc aatgcctgtg ggaggtggac tccctggatt agtactagac   3120
agaaaaggta caaaaatatt tcaaaccatt ctcacaactc tatatgtgtc tatgaccaga   3180
taactggaag accttctggt tatggactat gcgtatacac tctcccagat agttagaggc   3240
atatctaaga ggttaacata tatgatctta tccaaaatgg gtctcttggt gctagtgttt   3300
tacatcagac ttcactggct ttcatgtatt tccacaagtg ccaaacattt ctcatatcct   3360
tgctgtattc catagagcag tgttcctgct acctggaaca cttgattctt gaataactcc   3420
tgtttacctt tcagacaaac cctaaaggtt accacctcaa agaagtcttt atagaagcct   3480
catcatctta gacactctgt attgtttcct tcatcgtatt tacaacagac agatactgtg   3540
cacttactgc ctcacttaac gacagggata cgttctgaaa ggtgcatcat taggcggttt   3600
tgttgtgtga acatcacaga gtgttactta cacaaaccta aatgatacag cctactaaac   3660
acctaggcta tatgagcaat acagcctatt gctcttaggc ttcaaacttg tacgacatgt   3720
cactgtactg aatactgtag gcaactataa cacagtggta agtatattgt gtatctaaac   3780
aaacatagaa aaggtaatgc actgtactat gatgttacaa cagctaggat gttgctatca   3840
atagaaattt ttcagcttca ttttattttt atgggaccac ctttgtatat gtggttcatt   3900
gttggccgaa acaccattct gtggcacatg actatgtatt tattcctcat tattccttta   3960
atattcatct cttccaggag ggcatgtcat ggacaatctc tttttcttac cacaggtctt   4020
aggacctggc ctagcacctg gccaagaact actggcatac ctccttttat tgtgcttcaa   4080
tttattgtgc tttgcaaata ctgaattttt tacaagttga agatttgtgg cacctctgta   4140
accagcaagt ctattggtgc catttttca acatcatgtg cctgtttcct gtctcgctca   4200
tgtcacattt tggtaatttt cacaatatta aaaacttttt cattattatt a            4251
```

<210> SEQ ID NO 15
<211> LENGTH: 22
<212> TYPE: DNA
<213> ORGANISM: Artificial Sequence
<220> FEATURE:
<223> OTHER INFORMATION: Synthetic construct pSARS-F

<400> SEQUENCE: 15

```
gtgaaatggt catgtgtggc gg                                            22
```

<210> SEQ ID NO 16
<211> LENGTH: 26
<212> TYPE: DNA
<213> ORGANISM: Artificial Sequence
<220> FEATURE:
<223> OTHER INFORMATION: Synthetic construct pSARS-P

```
<400> SEQUENCE: 16

ccaggtggaa cctcatcagg agatgc                                  26


<210> SEQ ID NO 17
<211> LENGTH: 26
<212> TYPE: DNA
<213> ORGANISM: Artificial Sequence
<220> FEATURE:
<223> OTHER INFORMATION: Synthetic construct pSARS-R

<400> SEQUENCE: 17

tatgctaata gtgtttttaa catttg                                  26


<210> SEQ ID NO 18
<211> LENGTH: 26
<212> TYPE: DNA
<213> ORGANISM: Artificial Sequence
<220> FEATURE:
<223> OTHER INFORMATION: Synthetic construct E-Sarbeco_F

<400> SEQUENCE: 18

acaggtacgt taatagttaa tagcgt                                  26


<210> SEQ ID NO 19
<211> LENGTH: 50
<212> TYPE: DNA
<213> ORGANISM: Artificial Sequence
<220> FEATURE:
<223> OTHER INFORMATION: Synthetic construct E-Sarbeco_P/E-Sarbeco_R

<400> SEQUENCE: 19

acactagcca tccttactgc gcttcgattg tgtgcgtact gctgcaatat        50
```